United States Patent
Anno et al.

(10) Patent No.: US 9,351,694 B2
(45) Date of Patent: May 31, 2016

(54) COOLER, X-RAY COMPUTED TOMOGRAPHY APPARATUS, AND MAINTENANCE METHOD OF X-RAY COMPUTED TOMOGRAPHY APPARATUS

(71) Applicant: Toshiba Electron Tubes & Devices Co., Ltd., Otawara-shi (JP)

(72) Inventors: Hidero Anno, Otawara (JP); Tomonari Ishihara, Otawara (JP); Tetsuya Yonezawa, Yaita (JP); Harunobu Fukushima, Tokyo (JP); Chiharu Tadokoro, Machida (JP); Hitoshi Hattori, Yokohama (JP)

(73) Assignee: Toshiba Electron Tubes & Devices Co., Ltd., Otawara-shi (JP)

( * ) Notice: Subject to any disclaimer, the term of this patent is extended or adjusted under 35 U.S.C. 154(b) by 177 days.

(21) Appl. No.: 14/173,556

(22) Filed: Feb. 5, 2014

(65) Prior Publication Data

US 2014/0153689 A1    Jun. 5, 2014

Related U.S. Application Data

(63) Continuation of application No. PCT/JP2012/069744, filed on Aug. 2, 2012.

(30) Foreign Application Priority Data

Aug. 5, 2011   (JP) ................. 2011-172027
Sep. 27, 2011  (JP) ................. 2011-211486
Jun. 29, 2012  (JP) ................. 2012-147432
Jul. 31, 2012  (JP) ................. 2012-169319

(51) Int. Cl.
*H05G 1/02*     (2006.01)
*A61B 6/00*     (2006.01)

(52) U.S. Cl.
CPC .............. *A61B 6/4488* (2013.01); *H05G 1/025* (2013.01); *H01J 2235/1216* (2013.01); *H01J 2235/1283* (2013.01); *Y10T 29/49716* (2015.01)

(58) Field of Classification Search
CPC ....... A61B 6/4488; H05G 1/02; H05G 1/025; H01J 35/106; H01J 35/127; H01J 35/1283; H01J 2235/12; H01J 2235/1216–2235/1235; H01J 2235/127; H01J 2235/1283
USPC ..................... 378/4–20, 141, 193, 199, 200
See application file for complete search history.

(56) References Cited

U.S. PATENT DOCUMENTS 4,831,639 A    5/1989   Harke
5,956,383 A    9/1999   Kendall (Continued)

FOREIGN PATENT DOCUMENTS

CN       1891017 A     1/2007
CN     101091232 A    12/2007

(Continued)

OTHER PUBLICATIONS

International Preliminary Report on Patentability issued Feb. 20, 2014 in PCT/JP2012/069744.

(Continued)

*Primary Examiner* — Anastasia Midkiff
(74) *Attorney, Agent, or Firm* — Oblon, McClelland, Maier & Neustadt, L.L.P

(57) ABSTRACT

According to one embodiment, a cooler includes a casing, a radiator unit which is installed in a circulation path, where a coolant is circulated, and is configured to externally discharge heat of the coolant, and a fan unit housed in the casing to generate an air flow passing through the radiator unit. A windward side of the radiator unit is exposed to an outer side of the casing.

15 Claims, 23 Drawing Sheets

(56) References Cited

U.S. PATENT DOCUMENTS

| | | | |
|---|---|---|---|
| 6,491,428 B1 * | 12/2002 | Takanashi | A61B 6/035 378/199 |
| 7,416,333 B2 | 8/2008 | Zhang et al. | |
| 2004/0240619 A1 | 12/2004 | Kendall | |
| 2006/0002517 A1 | 1/2006 | Kendall | |
| 2009/0232281 A1 * | 9/2009 | Jimbo | A61B 6/035 378/199 |
| 2009/0279660 A1 | 11/2009 | Takamatsu et al. | |

FOREIGN PATENT DOCUMENTS

| | | |
|---|---|---|
| CN | 101091419 A | 12/2007 |
| CN | 101574265 A | 11/2009 |
| JP | 63-180010 | 11/1988 |
| JP | 7-194587 A | 8/1995 |
| JP | 09-056710 A | 3/1997 |
| JP | 10-179566 A | 7/1998 |
| JP | 2000-116639 A | 4/2000 |
| JP | 2001-137224 A | 5/2001 |
| JP | 2003-144425 A | 5/2003 |
| JP | 2004-344667 A | 12/2004 |
| JP | 2007-123212 A | 5/2007 |
| JP | 2007-514287 A | 5/2007 |
| JP | 2009-268830 A | 11/2009 |

OTHER PUBLICATIONS

Written Opinion issued Oct. 30, 2012 in PCT/JP2012/069744 (previously filed Feb. 5, 2014, submitting English translation only).
International Search Report mailed Oct. 30, 2012 for PCT/JP2012/069744 filed on Aug. 2, 2012 with English Translation.
International Written Opinion mailed Oct. 30, 2012 for PCT/JP2012/069744 filed on Aug. 2, 2012.
Combined Office Action and Search Report issued Jun. 3, 2015 in Chinese Patent Application No. 201280037927.1 (with English language translation).

* cited by examiner

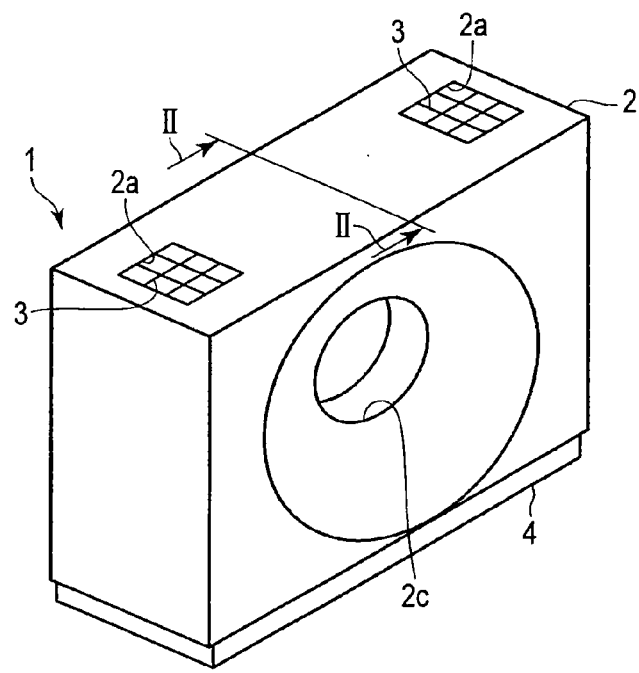
F I G. 1
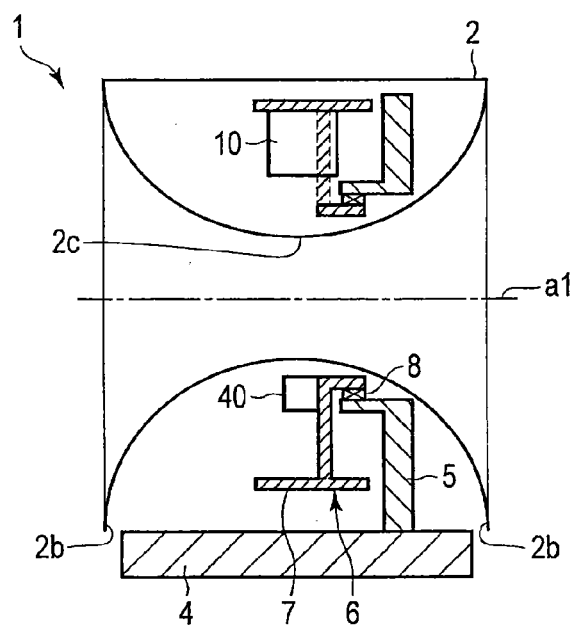
F I G. 2

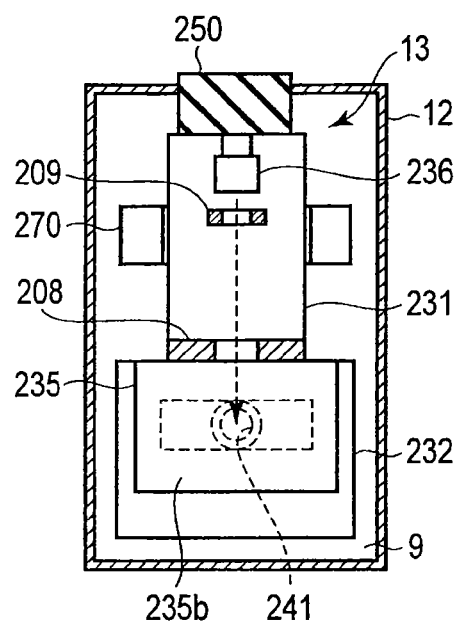
F I G. 8
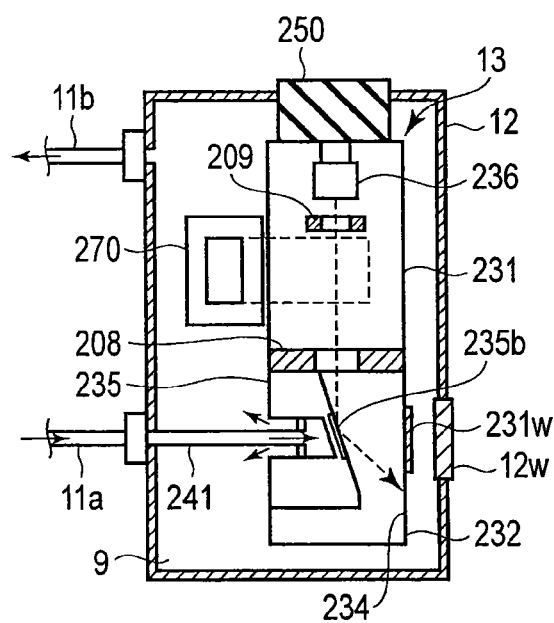
F I G. 9

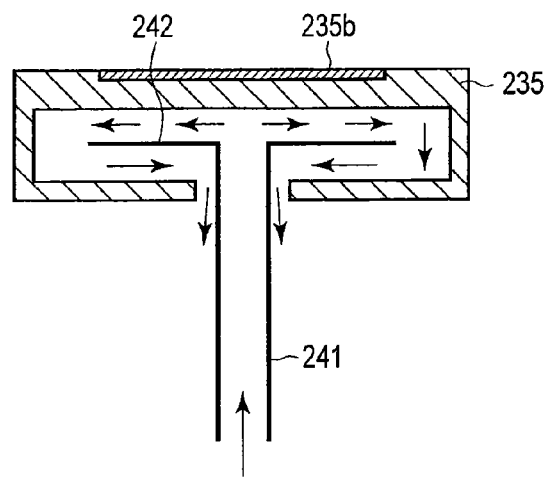
F I G. 10
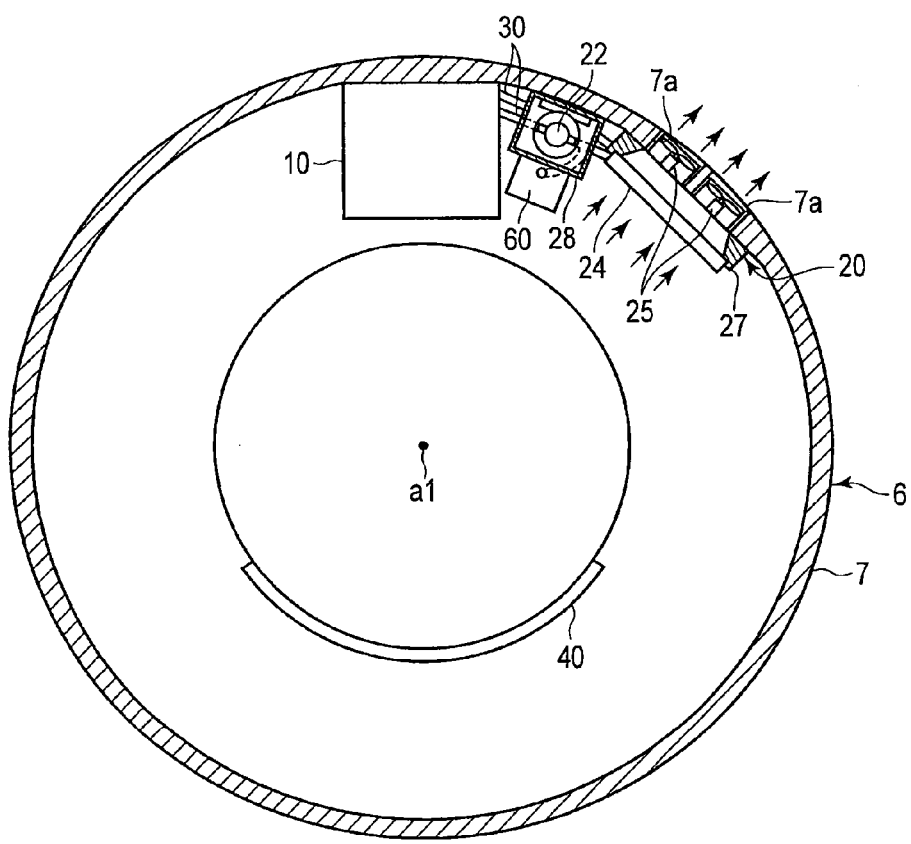
F I G. 11

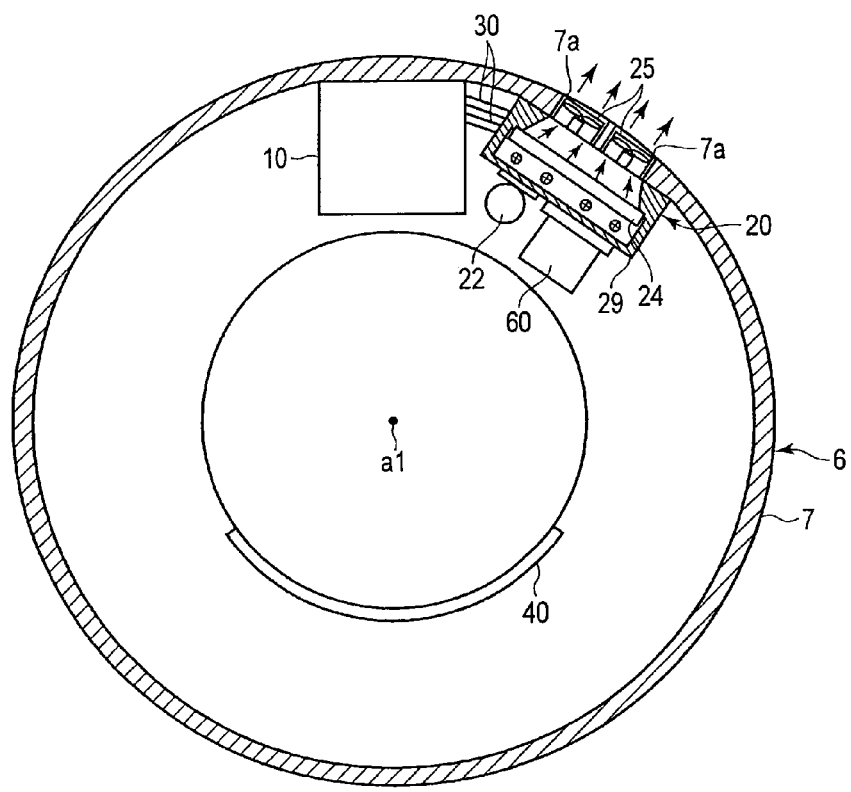
F I G. 12

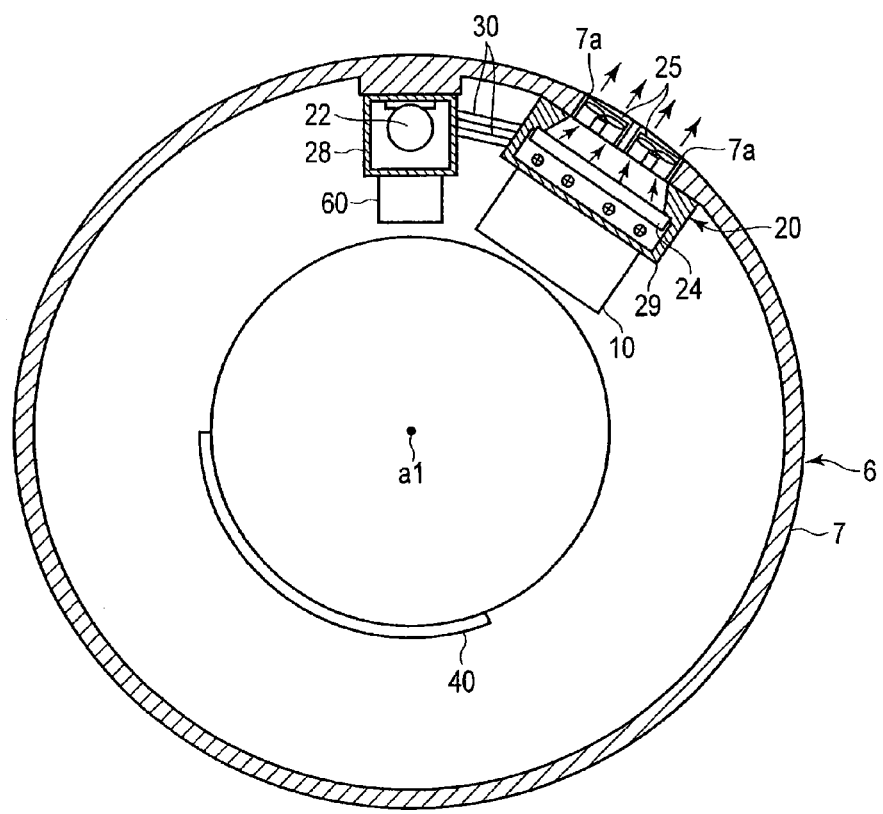
F I G. 13

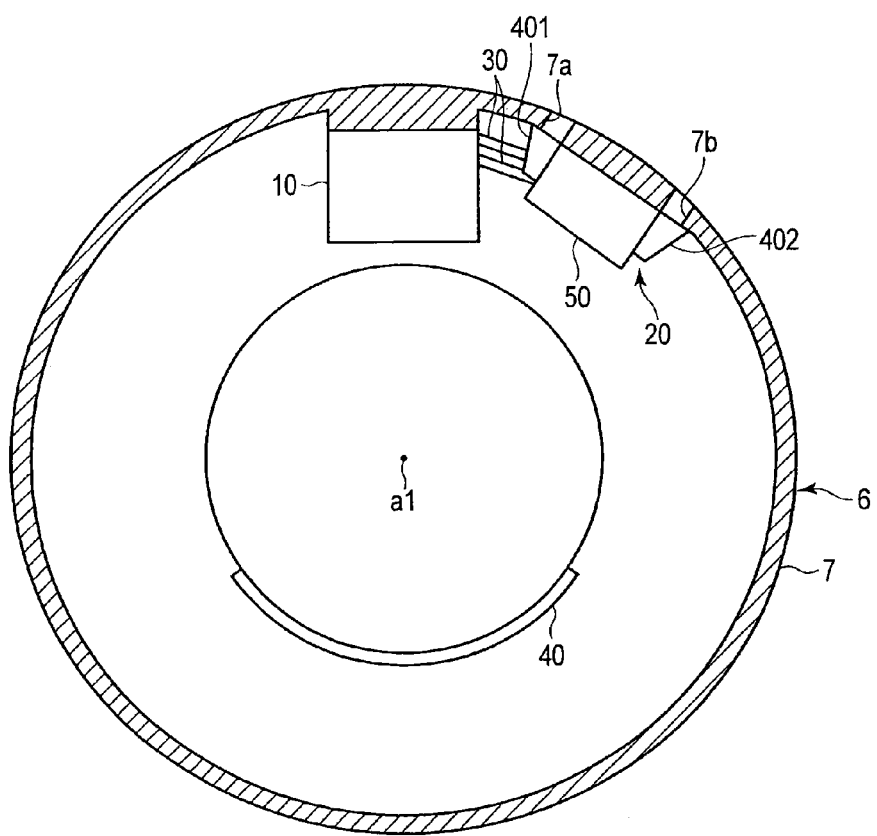
F I G. 14

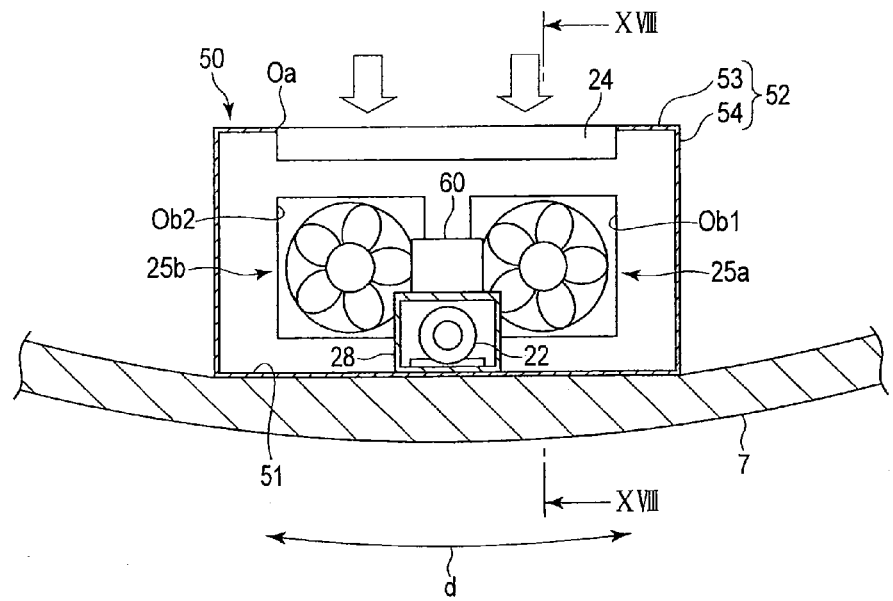
F I G. 17
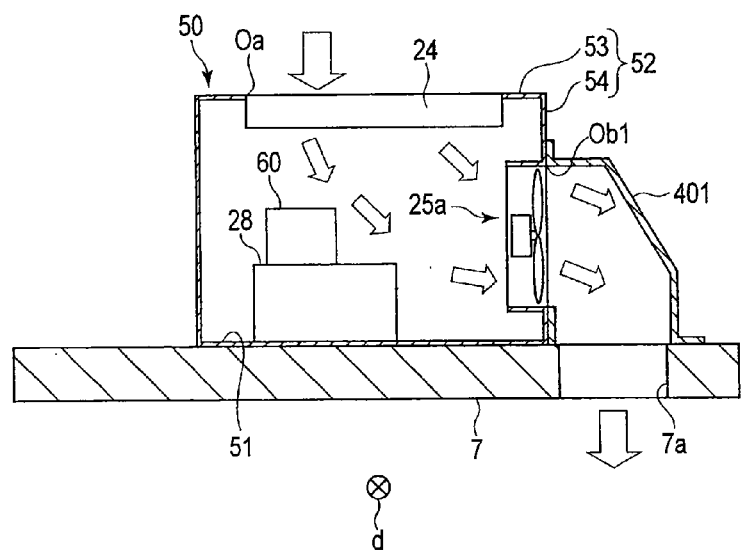
F I G. 18

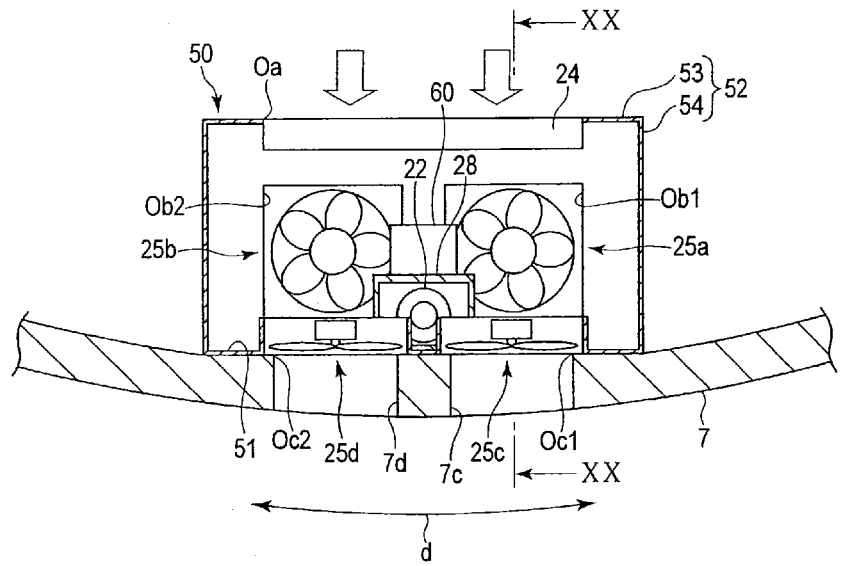
F I G. 19
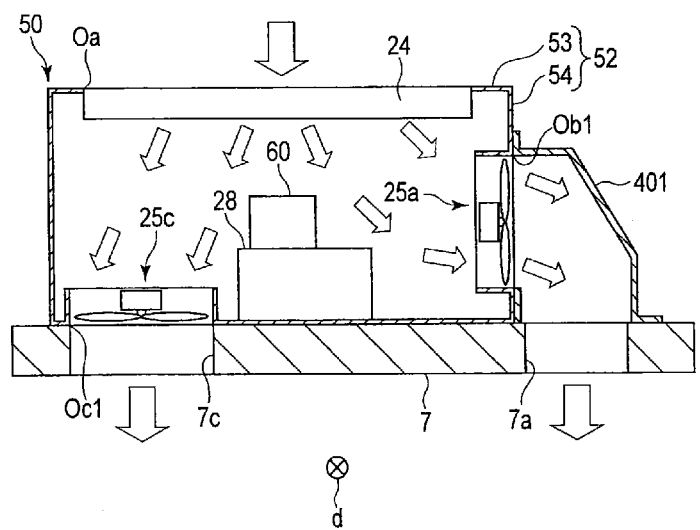
F I G. 20

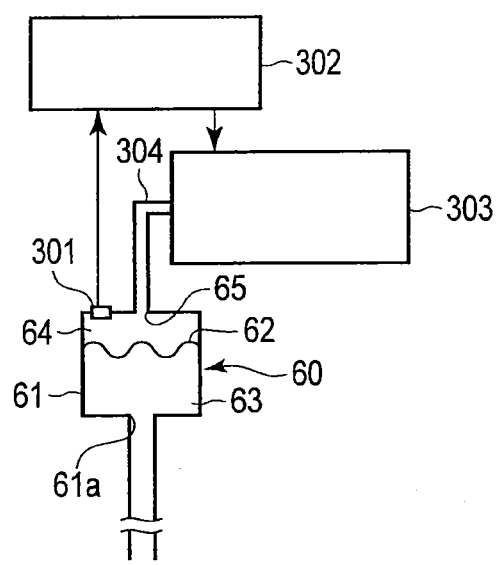
F I G. 26
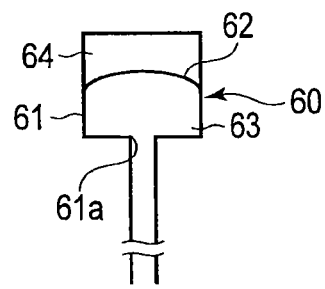
F I G. 27

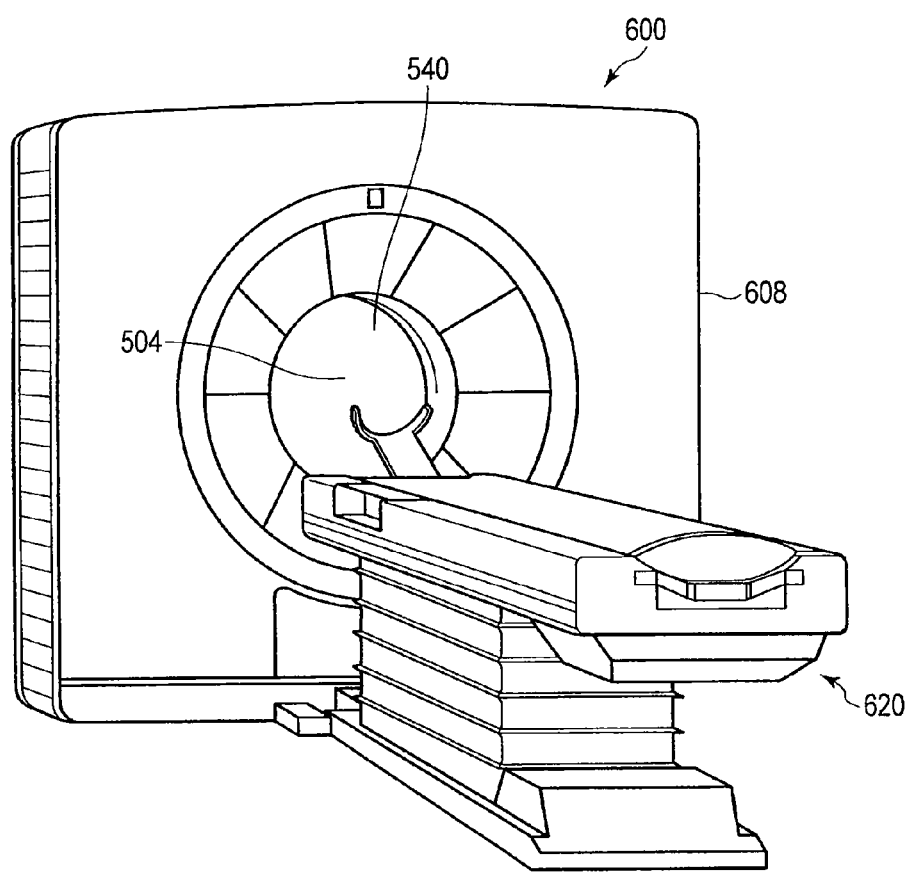
F I G. 29

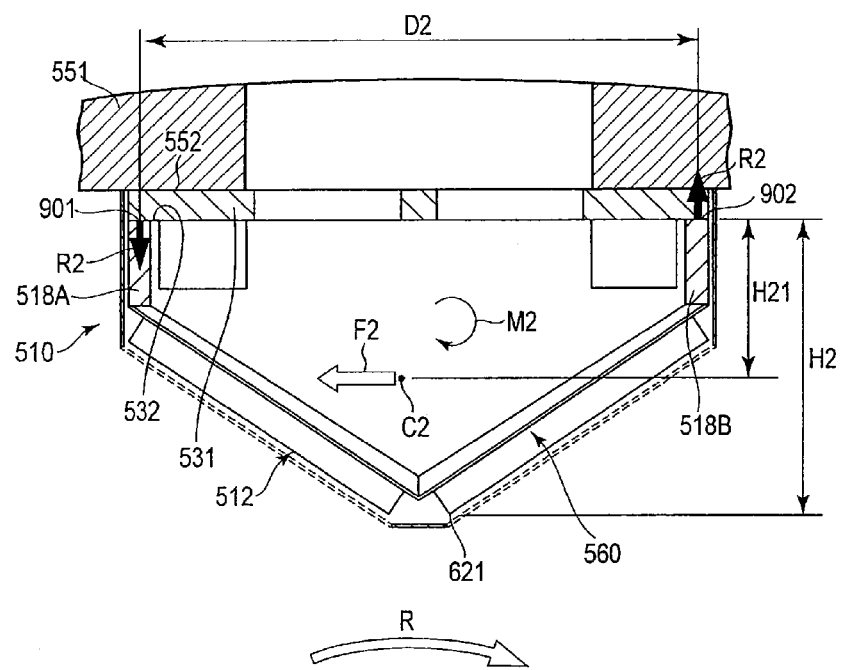
F I G. 33

COOLER, X-RAY COMPUTED TOMOGRAPHY APPARATUS, AND MAINTENANCE METHOD OF X-RAY COMPUTED TOMOGRAPHY APPARATUS

CROSS-REFERENCE TO RELATED APPLICATIONS

This application is a Continuation application of PCT Application No. PCT/JP2012/069744, filed Aug. 2, 2012 and based upon and claiming the benefit of priority from Japanese Patent Applications No. 2011-172027, filed Aug. 5, 2011; No. 2011-211486, filed Sep. 27, 2011; No. 2012-147432, filed Jun. 29, 2012; and No. 2012-169319, filed Jul. 31, 2012, the entire contents of all of which are incorporated herein by reference.

FIELD

Embodiments described herein relate generally to a cooler, an X-ray computed tomography apparatus, and a maintenance method of the X-ray computed tomography apparatus.

BACKGROUND

A gantry assembly of an X-ray computed tomography apparatus (hereinafter, referred to as an X-ray CT apparatus) includes a fixed frame, a rotary gantry frame rotatably supported by the fixed frame, and a casing that houses the fixed frame and the rotary gantry frame. The gantry assembly also includes an X-ray tube device mounted on the rotary gantry frame, an X-ray detector, a cooling unit (cooler), and the like.

Specifically, the rotary gantry frame has a ring-like frame. The X-ray tube device, the X-ray detector, the cooling unit, and the like are installed on an inner wall of the ring-like frame 10. Such units particularly demand strong fixation because they are relatively compact, have a large mass, and a high pressure applied to an installation surface.

In the structure described above, the rotary gantry frame is rotated at a high speed. As a result, even when a high centrifugal force is applied to the X-ray tube device, the cooling unit, and the like, it is possible to maintain strong fixation for frame by the X-ray tube device and the cooling unit.

The X-ray tube device and the cooling unit are connected through a circulation path where a coolant for transmitting heat generated in the X-ray tube is circulated. A heat generating source of the X-ray CT apparatus is the X-ray tube. For this reason, the heat generated by the X-ray tube is transmitted to the coolant, and the high-temperature coolant is delivered to the cooling unit. The cooling unit has a radiator and a fan unit. The coolant cooled by the cooling unit is returned to the X-ray tube.

The heat generated from the X-ray tube heats the air blowing from the fan unit. Then, the heated air remains inside the casing and raises the atmospheric temperature inside the casing. This may deteriorate cooling performance of the cooling unit or stability of the X-ray detector sensitivity.

For this reason, an opening is formed in the frame of the rotary gantry frame in order to discharge the air passing through the radiator to the outside of the frame through the opening. Here, in the casing, for example, an exhaust port is formed in the upper side, and an air intake is formed in the lower side. As a result, it is possible to discharge the air passing through the opening of the frame to the outside of the casing from the exhaust port and receive the new air into the inside of the casing from the air intake. Since the air inside the casing can be exchanged, it is possible to suppress an increase of the internal atmospheric temperature inside the casing.

BRIEF DESCRIPTION OF THE DRAWINGS

FIG. 1 is a perspective view illustrating an exterior of a gantry assembly of an X-ray CT apparatus according to a first embodiment.

FIG. 2 is a cross-sectional view illustrating the X-ray CT apparatus taken along a line II-II of FIG. 1.

FIG. 8 is a cross-sectional view illustrating an X-ray tube device of Example 2 of the X-ray CT apparatus according to the first embodiment.

FIG. 9 is another cross-sectional view illustrating the X-ray tube device of FIG. 8.

FIG. 10 is a partially enlarged cross-sectional view illustrating the X-ray tube device of FIGS. 8 and 9.

FIG. 11 is a front view illustrating a rotary gantry frame, and an X-ray tube device, a cooling unit and an X-ray detector mounted on the rotary gantry frame of an X-ray CT apparatus according to a second embodiment.

FIG. 12 is a front view illustrating a rotary gantry frame, and an X-ray tube device, a cooling unit and an X-ray detector mounted on the rotary gantry frame of an X-ray CT apparatus according to a third embodiment.

FIG. 13 is a front view illustrating a rotary gantry frame, and an X-ray tube device, a cooling unit and an X-ray detector mounted on the rotary gantry frame of an X-ray CT apparatus according to a fourth embodiment.

FIG. 14 is a front view illustrating a rotary gantry frame, and an X-ray tube device, a cooling unit and an X-ray detector mounted on the rotary gantry frame, a cooling unit, and an X-ray detector of an X-ray CT apparatus according to a fifth embodiment.

FIG. 17 is a partially enlarged schematic diagram illustrating an X-ray CT apparatus according to a seventh embodiment, including a frame, a circulation pump, a radiator, a fan unit, a mount, a casing, and an expansion mechanism.

FIG. 18 is a partial cross-sectional view illustrating the X-ray CT apparatus taken along a line XVIII-XVIII of FIG. 17.

FIG. 19 is a partially enlarged schematic diagram illustrating an X-ray CT apparatus according to an eighth embodiment, including a frame, a circulation pump, a radiator, a fan unit, a mount, a casing, and an expansion mechanism.

FIG. 20 is a partial cross-sectional view illustrating the X-ray CT apparatus taken along a line XX-XX of FIG. 19.

FIG. 26 is a schematic diagram illustrating another modification of the X-ray CT apparatus, including an empty tray, a pressure detector, a pressure control unit, and a pressure regulating mechanism.

FIG. 27 is a schematic diagram illustrating another modification of the X-ray CT apparatus including an expansion mechanism.

FIG. 29 is a perspective view schematically illustrating an X-ray CT apparatus according to a tenth embodiment.

FIG. 33 is a cross-sectional view schematically illustrating a characteristic of the cooler according to the tenth embodiment illustrated in FIG. 30.

DETAILED DESCRIPTION

Figure 3:
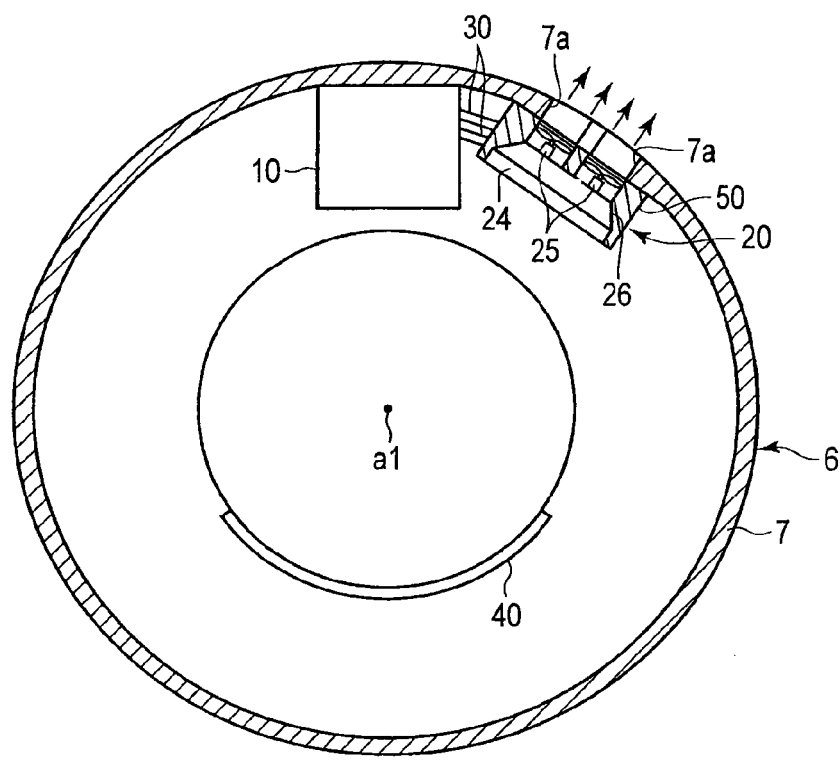
FIG. 3 is a front view illustrating the rotary gantry frame of FIG. 2, and an X-ray tube device, a cooling unit and an X-ray detector mounted on the rotary gantry frame.

In general, according to one embodiment, there is provided a cooler mounted on a rotor to cool an X-ray generator rotating around a rotational center axis along with the rotor. The cooler comprises: a casing comprising a base fixed to a cooler fixing surface of the rotor; a radiator unit which is installed in a circulation path, where a coolant is circulated, and covers a ventilation port provided in a portion other than the base of the casing to externally discharge heat of the coolant; and a fan unit housed in the casing to generate an air flow passing through the radiator unit. The air flow is a flow receding from the rotational center axis, and a windward side of the radiator unit is exposed to an outer side of the casing.

According to another embodiment, there is provided an X-ray computed tomography apparatus comprising: an X-ray tube device comprising a housing, and an X-ray tube housed in the housing, the X-ray tube including a cathode configured to discharge an electron beam, an anode target configured to discharge an X-ray by receiving the electron beam, and a vacuum envelope which stores the cathode and the anode target; a coolant where at least a part of heat generated in the X-ray tube is transferred; a circulation path where the coolant is circulated; a circulation pump installed in the circulation path to circulate the coolant; a radiator unit installed in the circulation path to externally discharge the heat of the coolant; a fan unit configured to generate an air flow passing through the radiator unit; an X-ray detector configured to detect the X-ray; and a rotary gantry frame including a ring-shaped frame portion rotating with respect to a rotation axis, the X-ray tube device, the circulation pump, the radiator unit, the fan unit, and the X-ray detector being installed in the rotary gantry frame. A windward side of the radiator unit is exposed in an inner wall side space of the frame portion.

According to still another embodiment, there is provided a method of maintaining an X-ray computed tomography apparatus, comprising: preparing the X-ray computed tomography apparatus comprising an X-ray tube device comprising a housing, and an X-ray tube housed in the housing, the X-ray tube including a cathode configured to discharge an electron beam, an anode target configured to discharge an X-ray by receiving the electron beam, and a vacuum envelope which stores the cathode and the anode target, a coolant where at least a part of heat generated in the X-ray tube is transferred, a circulation path where the coolant is circulated, a circulation pump installed in the circulation path to circulate the coolant, a radiator unit installed in the circulation path to externally discharge the heat of the coolant, a fan unit configured to generate an air flow passing through the radiator unit, an X-ray detector configured to detect the X-ray, a rotary gantry frame including a ring-shaped frame portion rotating with respect to a rotation axis, the X-ray tube device, the circulation pump, the radiator unit, the fan unit, and the X-ray detector being installed in the rotary gantry frame, and an expansion mechanism installed in the circulation path to absorb a volume change caused by a temperature change of the coolant, wherein a windward side of the radiator unit is exposed in an inner wall side space of the frame portion; dividing the housing, the radiator unit, the circulation pump, and the expansion mechanism connected to form the circulation path into a pair of channels using a pair of removable couplings; and installing another bellows mechanism in a channel that does not include the expansion mechanism using the removable coupling.

Hereinafter, an X-ray computed tomography apparatus according to a first embodiment will be described in detail with reference to the accompanying drawings. The X-ray computed tomography apparatus is referred to as an X-ray CT apparatus.

FIG. 1 is a perspective view illustrating an exterior of a gantry assembly of the X-ray CT apparatus according to the first embodiment. FIG. 2 is a cross-sectional view illustrating the X-ray CT apparatus taken along a line II-II of FIG. 1. FIG. 3 is a front view illustrating a rotary gantry frame, and an X-ray tube device, a cooling unit and an X-ray detector mounted on the rotary gantry frame of FIG. 2.

Referring to FIGS. 1 to 3, the X-ray CT apparatus 1 comprises a casing 2, a pedestal 4, a stationary gantry frame 5, a rotary gantry frame 6, a bearing member 8, an X-ray tube device 10, a cooling unit 20, and an X-ray detector 40.

The casing 2 houses a lot of members as described above. The casing 2 covers an exterior of the X-ray CT apparatus 1. The casing 2 includes an exhaust port 2a, an air intake 2b, and a gantry aperture 2c.

The exhaust port 2a is formed in an upper side of the casing 2. The exhaust port 2a is covered by a mesh-shaped cover 3 having an excellent air ventilation property. Although not illustrated in the drawings, the X-ray CT apparatus 1 further comprises a fan unit provided inside the casing 2 to face the cover 3. As a result, the air inside the casing 2 can be discharged to the outside of the casing 2 through the exhaust port 2a.

The air intake 2b is formed in a lower side of the casing 2. Here, the air intake 2b is located in a gap between the casing 2 and the pedestal 4. The fresh air from the outside of the casing 2 can be introduced into the inside of the casing 2 through the air intake 2b.

Using the aforementioned configuration, it is possible to exchange the air inside the casing 2 and thus suppress an increase of the internal air temperature of the casing 2.

An examinee is introduced into the gantry aperture 2c. Although not illustrated in the drawings, the X-ray CT apparatus 1 also has a couch where an examinee is laid.

The stationary gantry frame 5 is fixed to the pedestal 4. A bearing member (ball/roll bearing) 8 serving as a bearing mechanism is provided between the stationary gantry frame 5 and the rotary gantry frame 6.

The rotary gantry frame 6 is rotatably supported by the stationary gantry frame 5 by interposing the bearing member 8. The rotary gantry frame 6 is simply called a gantry and is rotatable with respect to a rotation axis (gantry assembly center) a1 of the rotary gantry frame 6. In order to rotate the rotary gantry frame 6 at a high speed, the X-ray CT apparatus employs, for example, a direct drive motor.

The rotary gantry frame 6 has an annulus frame 7 positioned in the outermost circumference. The frame 7 has an opening 7a. Here, a size of the opening 7a and the number of the opening 7 match the size and number of the fan units 25 described below.

The X-ray tube device 10, the cooling unit 20, and the X-ray detector 40 are provided in the rotary gantry frame 6. The X-ray tube device 10 and the cooling unit 20 are provided in the inner wall of the frame 7. Although not illustrated in the drawings, a high voltage generating power source or the like may be provided in the inner wall of the frame 7.

The X-ray tube device 10 and the cooling unit 20 are relatively compact with a high mass, and a high pressure is applied to an installation surface. Therefore, they are strongly fixed to the frame 7. As a result, even when the rotary gantry frame 6 is rotated at a high speed so that a high centrifugal force is applied to the X-ray tube device 10 and the cooling unit 20, the X-ray tube device 10 and the cooling unit 20 can maintain a strong fixation against the frame 7.

The X-ray tube device 10 serves as an X-ray generator to radiate an X-ray. The X-ray detector 40 faces the X-ray tube device 10 (X-ray tube) by interposing the rotation axis a1. The X-ray detector 40 includes a plurality of X-ray detection elements arranged, for example, in a circular arc shape. In the X-ray CT apparatus, a plurality of X-ray detectors 40 may also be arranged. The X-ray detector 40 detects the X-ray radiated from the X-ray tube device 10 and transmitted through an examinee and converts the detected X-ray into an electric signal.

Although not illustrated in the drawings, the X-ray CT apparatus 1 further includes a data acquisition device provided in the rotary gantry frame 6 to amplify the electric signal output from the X-ray detector 40 and convert an analog signal to a digital signal. In addition, although not illustrated in the drawings, the stationary gantry frame 5 may be provided with an apparatus configured to apply electric power, a control signal or the like to the X-ray tube device 10, the cooling unit 20, and the like. This apparatus may be installed in the X-ray tube device 10, the cooling unit 20, and the like provided in the rotary gantry frame 6 using a slip ring.

As the X-ray CT apparatus 1 enters into an operation state, the rotary gantry frame 6 is rotated with respect to the rotation axis a1. In this case, the X-ray tube device 10, the cooling unit 20, the X-ray detector 40, and the like are rotated in synchronization around an examinee. At the same time, an X-ray is radiated from the X-ray tube device 10.

The X-ray transmits through the examinee and is incident to the X-ray detector 40, so that the strength of the X-ray is detected by the X-ray detector 40. The detection signal detected by the X-ray detector 40 is amplified, for example, by the data acquisition device and is converted into a digital detection signal through the A/D conversion. The digital detection signal is supplied to a computer (not illustrated).

The computer computes an X-ray absorption rate in the interested area of the examinee base on the digital detection signal and establishes image data for creating a tomographic image of the examinee based on the computation result. The image data is transmitted to a display device or the like (not illustrated) and is displayed on a screen as the tomographic image.

As described above, the X-ray CT apparatus 1 acquires the strength, that is, projection data, of the X-ray transmitting through every point on an examination cross-section of the examinee across various angles, for example, across a range of 360° while the X-ray tube device 10 and the X-ray detector 40 are rotated around the examinee. In addition, the tomographic image is created by a data restructuring program stored in advance based on this projection data.

Figure 4:
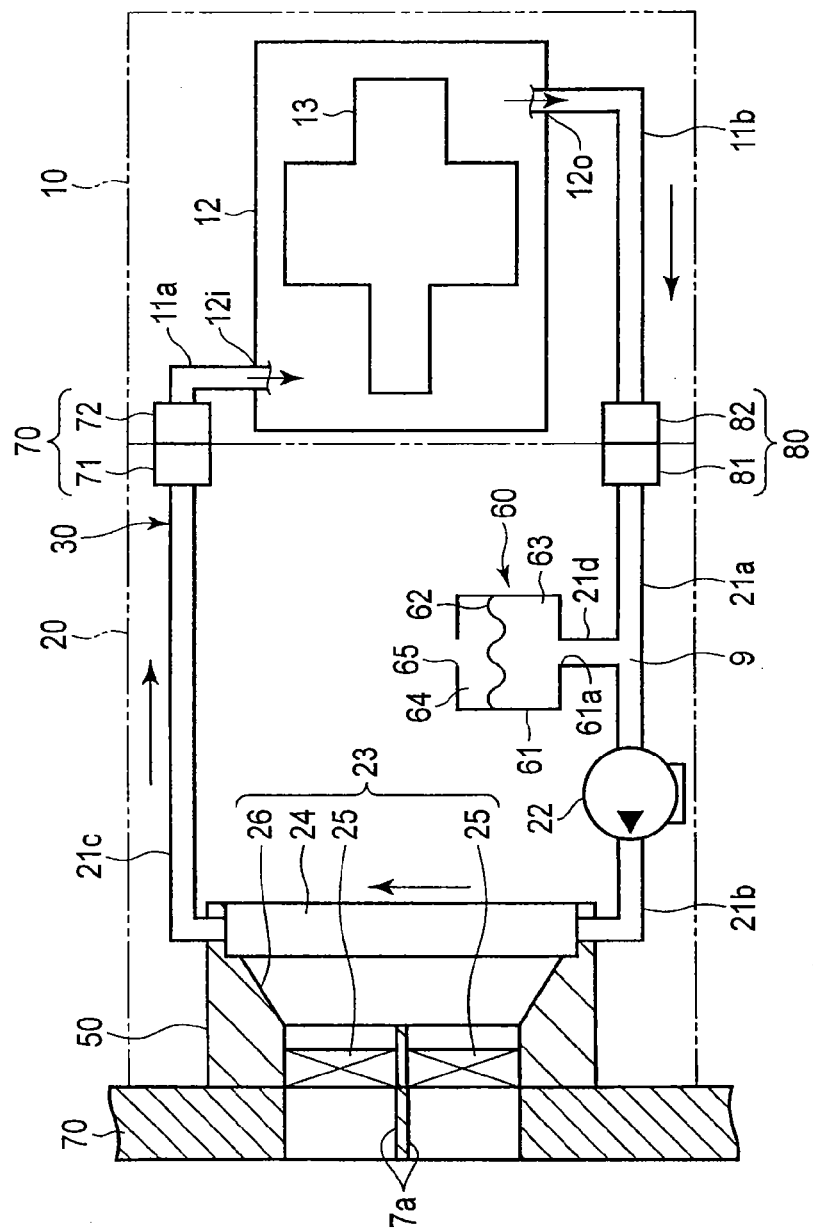
FIG. 4 is a conceptual diagram illustrating the X-ray tube device and the cooling unit.

FIG. 4 is a conceptual diagram illustrating the X-ray tube device 10 and the cooling unit 20. In FIG. 4, a positional relationship between the opening 7a and a heat exchanger 23 described below is exaggeratingly illustrated.

As illustrated in FIGS. 3 and 4, the X-ray tube device 10 has a housing 12 and an X-ray tube 13 housed in the housing 12. The housing 12 (X-ray tube device 10) is independently and directly or indirectly installed and fixed to the rotary gantry frame 6. Here, the housing 12 is directly installed on the inner wall of the frame 7.

The X-ray tube 13 includes a cathode that emits an electron beam, an anode target that emits an X-ray by receiving the radiated electron beam, and a vacuum envelope that stores the cathode and the anode target. Here, the X-ray CT apparatus 1 has a coolant 9. At least a part of the heat generated from the X-ray tube 13 is transferred to the coolant 9.

The X-ray tube device 10 has conduits 11a and 11b. One end of the conduit 11a is installed in a coolant intake 12i of the housing 12 in an air-tight manner, and the other end is installed in a socket 72 in an air-tight manner. One end of the conduit 11b is installed in the coolant discharge port 12o of the housing 12 in an air-tight manner, and the other end is installed a socket 82 in an air-tight manner. The conduits 11a and 11b constitute a part of a circulation path 30 where the coolant 9 is circulated.

When the heat transfer surface is an outer surface of the X-ray tube 13, the coolant 9 is stored in the housing 12. The housing 12 forms a part of the circulation path 30 along with the conduits 11a and 11b. In addition, as the coolant 9 circulates through the heat transfer surface of the X-ray tube 13, it is possible to cool the X-ray tube 13, particularly, the anode target described below.

When the heat transfer surface is positioned in the inside of the X-ray tube 13, the conduit 11a and the X-ray tube 13 are connected to each other directly or indirectly using a coupling. Alternatively, the conduit 11b and the X-ray tube 13 are connected to each other directly or indirectly using a coupling. A space between the housing 12 and the X-ray tube 13 form a part of the circulation path 30 along with the conduits 11a and 11b. As a result, as the coolant 9 is circulated through the heat transfer surface inside of the X-ray tube 13, it is possible to cool the X-ray tube 13, particularly, the anode target described below.

Alternatively, when the heat transfer surface is positioned inside the X-ray tube 13, and both the conduits 11a and 11b are connected to the X-ray tube 13, the coolant may be stored in the housing 12, or the coolant may not be stored in the housing 12. In this case, a type of the coolant stored in the housing 12 may different from that of the coolant 9. The inside of the X-ray tube 13 forms a part of the circulation path 30 along with the conduits 11a and 11b. As a result, as the coolant 9 circulates through the heat transfer surface inside the X-ray tube 13, it is possible to cool the X-ray tube 13, particularly, the anode target described below.

The cooling unit 20 includes conduits 21a, 21b, 21c, and 21d, a circulation pump 22, a heat exchanger 23, and an expansion mechanism 60. One end of the conduit 21a is installed in the plug 81 in an air-tight manner. One end of the conduit 21c is installed in the plug 71 in an air-tight manner. One end of the conduit 21d is installed in the conduit 21a in an air-tight manner. The conduits 21a, 21b, 21c, and 21d constitute a part of the circulation path 30.

The circulation pump 22 is independently installed in and fixed to the inner wall of the frame 7 in a direct or indirect manner. Here, the circulation pump 22 is directly installed in the inner wall of the frame 7. The circulation pump 22 is installed in the circulation path 30. Here, the circulation pump 22 is installed between the conduits 21a and 21b in an air-tight manner. The circulation pump 22 discharges the coolant 9 to the conduit 21b and receives the coolant 9 from the conduit 21a. The circulation pump 22 can circulate the coolant 9 in the circulation path 30.

The heat exchanger 23 is installed in the circulation path 30 and discharges the heat of the coolant 9 to the outside. The heat exchanger 23 includes a radiator 24, a fan unit 25, and a duct 26.

The radiator 24 is installed in the circulation path 30. The radiator 24 includes a plurality of heat-radiating pipes (not illustrated) connected between the conduits 21b and 21c, where the coolant flows, and a plurality of heat-radiating fins (not illustrated) provided in the heat-radiating pipes. The radiator 24 can radiate the heat of the coolant 9 to the outside. Specifically, the radiator 24 has a fin-tube type structure approximately in a panel shape, in which a plurality of fins having a circular or flat cross sections for enlarging the surface area making contact with the air are installed in the tube where the coolant flows. The radiator 24 includes a front side corresponding to a windward side of the air flow passing through the radiator and a rear side corresponding to a leeward side. For example, when the flat fins are installed in the tube in parallel with the longitudinal direction of the tube, the gaps between the neighboring fins serve as a flow path of the air. In addition, for example, when a plurality of flat tubes arranged with an equal interval and corrugated plate-like fins provided in gaps therebetween are installed such that each top portion of the fins is bonded to each flat side face of the flat tubes, the gaps between the fins and the flat side faces serve as a flow path of the air.

The fan unit 25 is positioned to face the opening 7a and the rear side of the radiator 24. A distance from the rotation axis a1 to the fan unit 25 is longer than a distance between the rotation axis a1 to the radiator 24. The fan unit 25 can generate an air flow passing through the radiator 24 from the front side to the rear side. The fan unit 25 can discharge the air passing through the radiator 24 to the outside of the rotary gantry frame 6 (frame 7) through the opening 7a.

As described above, the heat exchanger 23 can discharge the heat of the coolant 9 to the outside. In addition, since the air passing through the radiator 24 can be discharged to the outside of the rotary gantry frame 6, it is possible to suppress an increase of the internal air temperature of the rotary gantry frame 6.

The duct 26 is positioned between the radiator 24 and the fan unit 25. The duct 26 surrounds a periphery of the radiator 24 and a periphery of the fan unit 25. The duct 26 can guide the air flow around the radiator 24 to the fan unit 25. Since the heated air can be efficiently guided to the fan unit 25 by flowing the air through the radiator 24, it is possible to further suppress an increase of the air temperature inside the rotary gantry frame 6 (in the space surrounded by the rotary gantry frame 6 and the casing 2). As a result, it is possible to improve cooling performance of the heat exchanger 23 or sensitivity stability of the X-ray detector 40.

The cooling unit 20 further includes a casing 50 installed in the rotary gantry frame 6. The casing 50 is installed and fixed to the inner wall of the frame 7. The casing 50 is formed of, for example, a sheet metal. The casing 50 is designed to have a mechanical strength capable of enduring a centrifugal force applied by rotating the rotary gantry frame 6.

The radiator 24, the fan unit 25, and the duct 26 are housed and unitized in the casing 50. The casing 50 is opened to the outside to expose the radiator 24 and the fan unit 25.

The radiator 24, the fan unit 25, and the duct 26 are directly or indirectly installed and fixed to the rotary gantry frame 6. Here, the radiator 24, the fan unit 25, and the duct 26 are indirectly installed in the inner wall of the frame 7 using the casing 50.

The empty tray 60 is directly or indirectly installed in the rotary gantry frame 6. Here, the empty tray 60 is directly installed in the frame 7 independently from the housing 12, the circulation pump 22, the radiator 24, the fan unit 25, and the like. The empty tray 60 is installed in the circulation path 30.

The expansion mechanism 60 includes a vessel 61 having an opening 61a. The opening 61a communicates with the conduit 21d in an air-tight manner. The expansion mechanism 60 includes a bellows 62 as an elastic diaphragm that partitions the inside of the vessel 61 into a first space 63 connected to the opening 61a and a second space 64. A ventilation port 65 connected to the second space 64 is formed in the vessel 61. The second space 64 is opened to the atmospheric air in order to allow the air to access the ventilation port 65. The bellows 62 is installed in the vessel 61 in a liquid-tight manner. The bellows 62 is expandable and/or retractable. Here, the bellows 62 is formed of rubber. The bellows 62 can absorb a volume change caused by a temperature change of the coolant 9 (volume expansion and contraction). The bellows 62 is preferably formed of a material having a gas-impermeable property.

The plug 71 and the socket 72 constitute a coupler 70 as a removable coupling, and the plug 81 and the socket 82 constitute a coupler 80 as a removable coupling. The couplers 70 and 80 can switch between a plug-socket connected state (fixed state) and a plug-socket disconnected state. In the connected state, the couplers 70 and 80 are connected to each other in an air-tight and liquid-tight manner. The couplers 70 and 80 have a shut-off valve. In the disconnected state of the couplers 70 and 80, the plugs 71 and 81 and the sockets 72 and 82 have a structure capable of preventing an external leakage of a liquid (coolant 9) and an intrusion of the air. As the couplers 70 and 80 switch to the disconnected state, the air flow can be divided into two channels. Therefore, it is possible to separate the X-ray tube device 10 and the cooling unit 20.

It is difficult to absorb the volume change of the coolant 9 using the X-ray tube device 10 having the disconnected state.

In this regard, by forming the conduits 11a and 11b with a rubber hose, it is possible to provide a functionality of absorbing a volume change of the coolant 9 using the conduits 11a and 11b. However, in some cases, it is difficult to sufficiently absorb the volume change of the coolant 9 only using the conduits 11a and 11b. In this case, an empty tray is preferably installed in the X-ray tube device 10 having the disconnected state.

Figure 5:
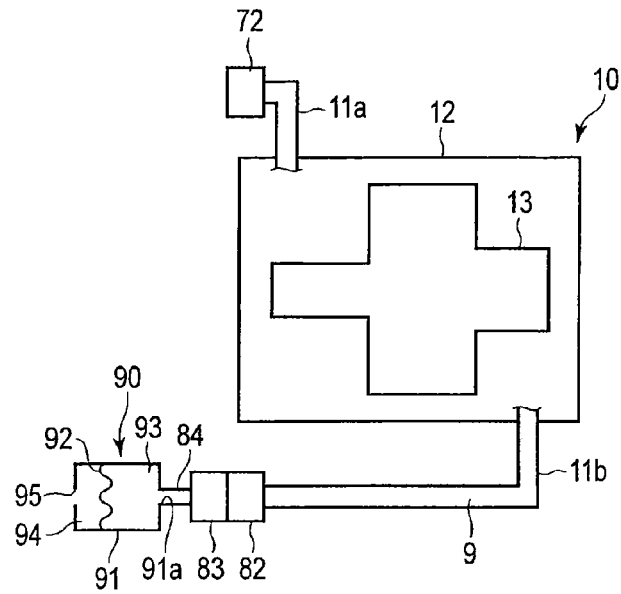
FIG. 5 is a schematic diagram illustrating a disconnected state of the X-ray tube device of FIG. 4.

FIG. 5 is a schematic diagram illustrating a disconnected state of the X-ray tube device 10 of FIG. 4.

As illustrated in FIG. 5, the expansion mechanism 90 is installed in the X-ray tube device 10. The expansion mechanism 90 is installed in the X-ray tube device 10 using the plug 83 and the conduit 84 connected to each other in an air-tight and liquid-tight manner. The plug 83 and the socket 82 constitute a coupler as a removable coupling and are connected to each other in an air-tight and liquid-tight manner in the connected state.

The expansion mechanism 90 includes a vessel 91 having an opening 91a. The opening 91a communicates to the conduit 84 in an air-tight manner. The empty tray 90 has a bellows 92 that partitions the inside of the vessel 91 into a first space 93 connected to the opening 91a and a second space 94. The vessel 91 is provided with a ventilation port 95 connected to the second space 94. The second space 94 is opened to the atmospheric air in order to allow the air to access the ventilation port 95. It is noted that the ventilation port 95 may not be formed in the vessel 91. In this case, the second space 94 becomes a hermetically sealed space.

The bellows 92 is installed in the vessel 91 in a liquid-tight manner. The bellows 92 is expandable and/or retractable. Here, the bellows 92 is formed of rubber. The bellows 92 can absorb a volume change caused by a temperature change (volume expansion and contraction) of the coolant 9. The bellows 92 is preferably formed of a material exhibiting a gas-impermeable property.

As a result, in the X-ray tube device 10 having a disconnected state (after disconnection), it is possible to prevent an external leakage of the liquid (coolant 9) and intrusion of the air.

Figure 6:
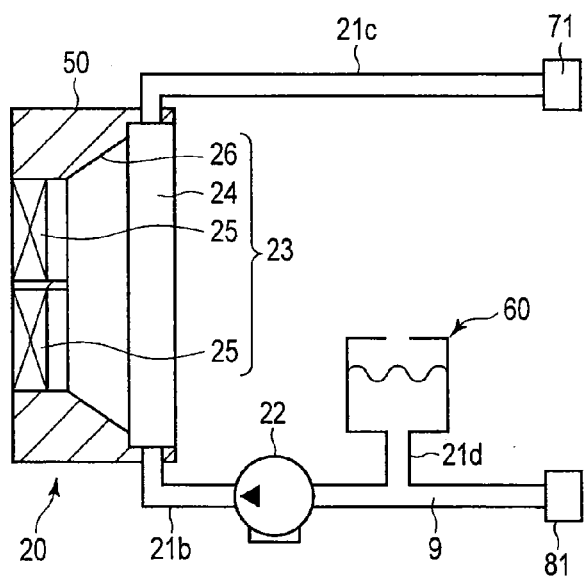
FIG. 6 is a schematic diagram illustrating a disconnected state of the cooling unit of FIG. 4.

FIG. 6 is a schematic diagram illustrating a disconnected state of the cooling unit 20 of FIG. 4.

Meanwhile, as illustrated in FIG. 6, the cooling unit 20 of the disconnected state has an empty tray 60. For this reason, without adding something to the cooling unit 20, it is possible to prevent an external leakage of the liquid (coolant 9) and intrusion of the air in the cooling unit 20 of the disconnected state.

Figure 7:
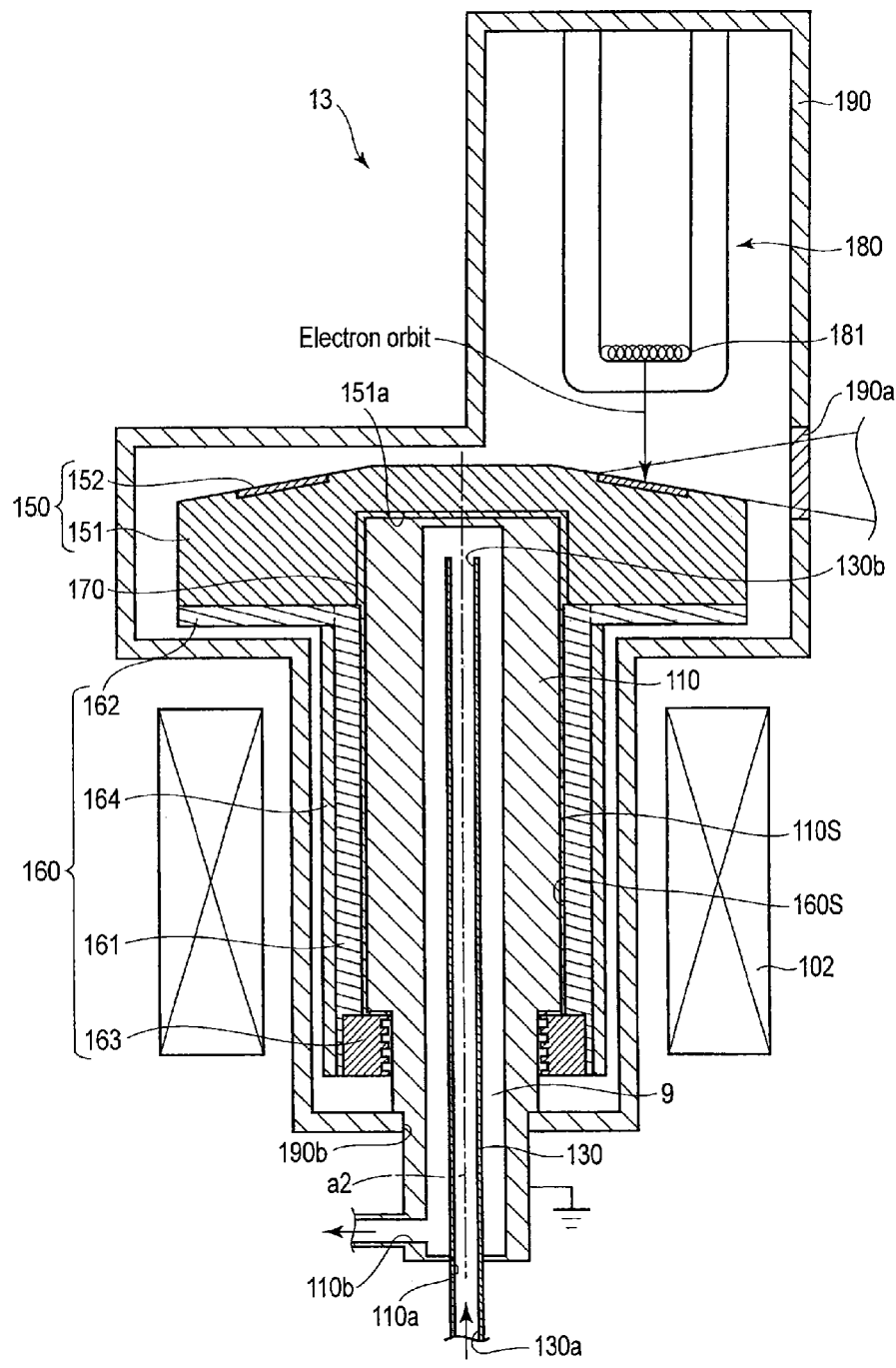
FIG. 7 is a cross-sectional view illustrating an X-ray tube device of Example 1 of the X-ray CT apparatus according to the first embodiment.

Here, an X-ray tube device of Examples 1 and 2 as an example of the X-ray tube device 10 of the X-ray CT apparatus according to the first embodiment will be described. First, the X-ray tube device 10 of Example 1 will be described. FIG. 7 is a cross-sectional view illustrating the X-ray tube device 10 of Example 1.

As illustrated in FIG. 7, the X-ray tube device 10 is a rotary anode type X-ray tube device, and the X-ray tube 13 is a rotary anode type X-ray tube. The X-ray tube device 10 has a stator coil 102 as a coil for generating a magnetic field in addition to the X-ray tube 13. Although not illustrated in the drawings, the housing 12 (FIG. 4) houses the X-ray tube 13 and the stator coil 102.

The X-ray tube 13 comprises a fixed shaft 110 as a stator, a tube 130, an anode target 150, a rotor 160, a liquid metal 170 as a lubricant, a cathode 180, and a vacuum envelope 190. A dynamic pressure slide bearing is applied to the X-ray tube 13.

The fixed shaft 110 is formed in a cylindrical shape extending along a rotation axis a2 serving as a center axis. One end of the fixed shaft 110 is closed. The fixed shaft 110 has a bearing surface 110S in a side face extending from the one end. The fixed shaft 110 is formed of an iron (Fe) alloy, a molibdemum (Mo) alloy, and the like. The coolant 9 is filled in the inside of the fixed shaft 110. The fixed shaft 110 internally has a fluid path where the coolant 9 flows. The fixed shaft 110 has an outlet port 110b for discharging the coolant 9 to the outside in the other end.

The tube 130 is provided in the inside of the fixed shaft 110 and forms a fluid path along with the fixed shaft. One end of the tube 130 extends to the outside of the fixed shaft 110 through the opening 110a formed in the other end of the fixed shaft 110. The tube 130 is closely fixed to the opening 110a.

The tube 130 has an intake 130a that introduces the coolant 9 to the inside of the tube 130 and an discharge port 130b that discharges the coolant 9 to the inside of the fixed shaft 110. The intake 130a is located outside the fixed shaft 110. The outlet port 130b is located in one end of the fixed shaft 110 by interposing a gap.

The intake 130a is connected to the conduit 11a directly or indirectly using a coupling, and the discharge port 110b is opened to the inside of the housing 12. Alternatively, the intake 130a is opened to the housing 12, and the discharge port 110b is connected to the conduit 11b directly or indirectly using a coupling.

As described above, the coolant 9 from the outside of the X-ray tube 13 is introduced from the intake 130a, passes through the tube 130, and is discharged to the inside of the fixed shaft 110. Then, the coolant 9 passes through a pass between the fixed shaft 110 and the tube 130 and is discharged to the outside of the X-ray tube 13 from the discharge port 110b.

The anode target 150 includes an anode 151 and a target layer 152 provided in a part of an external surface of the anode. The anode 151 is formed in a disk shape and is provided coaxially with the fixed shaft 110. The anode 151 is formed of a molybdenum (Mo) alloy and the like. The anode 151 has a concave portion 151a along the rotation axis a2. The concave portion 151a is formed in a hollow of the disk shape. One end of the fixed shaft 110 is fitted to the concave portion 151a. The concave portion 151a is formed in one end of the fixed shaft 110 with a gap. The target layer 152 is formed in a wheel shape and is formed of a tungsten (W) alloy and the like. A surface of the target layer 152 serves as an electron collision surface.

The rotor 160 is formed in a cylindrical shape having a diameter larger than that of the fixed shaft 110. The rotor 160 is provided coaxially with the fixed shaft 110 and the anode target 150. The rotor 160 is shorter than the fixed shaft 110.

The rotor 160 is formed of iron (Fe), molybdenum (Mo), and the like. More specifically, the rotor 160 includes a cylindrical portion 161, a ring 162 integrated with the cylindrical portion to surround a side face of one end of the cylindrical portion 161, a sealing portion 163 provided in the other end of the cylindrical portion 161, and a cylindrical portion 164.

The cylindrical portion 161 surrounds the side face of the fixed shaft 110. The cylindrical portion 161 has a bearing surface 160S facing the bearing surface 110S with a gap in the inner surface. One end of the rotor 160, that is, one end of the cylindrical portion 161 and the ring 162 are bonded to the anode target 150. The rotor 160 is provided rotatably along with the anode target 150 with respect to the fixed shaft 110.

The sealing portion 163 is positioned opposite to the ring 162 (one end) with respect to the bearing surface 160S. The sealing portion 163 is bonded to the other end of the cylindrical portion 161. The sealing portion 163 is formed in a ring shape and is provided across the entire side face of the fixed shaft 110 with a gap. The cylindrical portion 164 is bonded to side face of the cylindrical portion 161 and is fixed to the cylindrical portion 161. The cylindrical portion 164 is formed of, for example, copper (Cu).

The liquid metal 170 is filled in a gap between the one end of the fixed shaft 110 and the concave portion 151*a* and a gap between the fixed shaft 110 (bearing surface 110S) and the cylindrical portion 161 (bearing surface 160S). It is noted that such gaps are entirely connected to each other. In this embodiment, the liquid metal 170 is a gallium-indium-tin (GaInSn) alloy.

The gap (clearance) between the sealing portion 163 and the fixed shaft 110 in a direction perpendicular to the rotation axis a2 is set to a value by which rotation of the rotor 160 can be maintained, and a leakage of the liquid metal 170 can be suppressed. As described above, the gap is set to at least 500 μm or shorter. For this reason, the sealing portion 163 serves as a labyrinth seal ring.

The sealing portion 163 includes a plurality of storage portion formed by hollowing the inner side in a circular frame shape. The storage portion stores the leaking liquid metal 170 when the liquid metal 170 leaks from the gap.

The cathode 180 is arranged to face the target layer 252 of the anode target 150 with an interval. The cathode 180 has a filament 181 that emits electrons.

The vacuum envelope 190 houses the fixed shaft 110, the tube 130, the anode target 150, the rotor 160, the liquid metal 170 and the cathode 180. The vacuum envelope 190 has an X-ray transmission window 190*a* and an opening 190*b*. The X-ray transmission window 190*a* faces the target layer 152 in a direction perpendicular to the rotation axis a2. The other end of the fixed shaft 110 is exposed to the outside of the vacuum envelope 190 through the opening 190*b*. The opening 190*b* closely fixes the fixed shaft 110.

The cathode 180 is installed in the inner wall of the vacuum envelope 190. The vacuum envelope 190 is hermetically sealed. The inside of the vacuum envelope 190 is maintained in a vacuum state.

The stator coil 102 is provided to face the side face of the rotor 160, more specifically, the side face of the cylindrical portion 164 and surround the outer side of the vacuum envelope 190. The stator coil 102 has a ring shape.

Here, an operation state of the X-ray tube 13 and the stator coil 102 will be described. Since the stator coil 102 generates a magnetic field applied to the rotor 160 (particularly, the cylindrical portion 164), the rotor is rotated. As a result, the anode target 150 is also rotated. In addition, a negative voltage (high voltage) is applied to the cathode 180, and the anode target 150 is set to a ground voltage.

As a result, a voltage difference is generated between the cathode 180 and the anode target 150. For this reason, as an electron is discharged from the cathode 180, this electron is accelerated and collides with the target layer 152. That is, the cathode 180 irradiates an electron beam onto the target layer 152. As a result, the target layer 152 discharges an X-ray when an electron collides. The discharged X-ray is discharged to the outside of the vacuum envelope 190 and further the outside of the housing 12 through the X-ray transmission window 190*a*. The X-ray tube device 10 of Example 1 is formed in this manner.

Next, an X-ray tube device 10 of Example 2 will be described. FIG. 8 is a cross-sectional view illustrating an X-ray tube device of Example 2. FIG. 9 is another cross-sectional view illustrating the X-ray tube device of FIG. 8.

FIG. 10 is a partially enlarged cross-sectional view illustrating the X-ray tube device of FIGS. 8 and 9.

Referring to FIGS. 8 to 10, the X-ray tube device 10 is a stationary anode type X-ray tube device, and the X-ray tube 13 is a stationary anode type X-ray tube. The X-ray tube 13 has a vacuum envelope 231. The vacuum envelope 231 includes a vacuum container 232 and an insulation member 250. In this embodiment, the insulation member 250 serves as a high-voltage insulation member. A cathode 236 is installed in the insulation member 250, and the insulation member 250 forms a part of the vacuum envelope 231.

The anode target 235 forms a part of the vacuum envelope 231. The anode target 235 is opened to the outside of the vacuum envelope 231 with a small opening and is formed in a vessel shape bulging in the vicinity of the target surface 235*b*. The anode target 235, the cathode 236, a focusing electrode 209, and an accelerating electrode 208 are housed in the vacuum envelope 231. The anode target 235 is connected to a voltage supply line. The anode target 235 and the accelerating electrode 208 are set to a ground voltage. A part of the vacuum container 232 facing the cathode 236 and the focusing electrode 209 is formed in a cylindrical shape. A high negative voltage is applied to the cathode 236. A high negative regulated voltage is supplied to the focusing electrode 209. The inside of the vacuum envelope 231 has a vacuum state. A metal surface portion 234 is provided in the inner side of the vacuum container 232 including a vacuum-side surface of the X-ray radiation window 231*w* and is set to a ground voltage.

The X-ray tube 13 further includes a tube 241 and a ring 242. The tube 241 is formed of a metal. One end of the tube 241 is inserted into the inside of the anode target 235. The ring 242 is provided inside the anode target 235. The ring 242 is integrated with the tube 241 to surround a side face of one end of the tube 241. The ring 242 is provided in the anode target 235 with a gap. The other end of the tube 241 forms a coolant intake and is connected to the conduit 11*a*. The opening of the anode target 235 forms a coolant discharge port with the tube 241. For this reason, the inside of the housing 12 is filled with the coolant 9. The housing 12 has an X-ray radiation window 12*w* facing the X-ray radiation window 231*w*.

A deflecting module 270 is housed in the housing 12. The deflecting module 270 is a magnetic deflecting module and is positioned to surround a locus of the electron beam in the outside of the vacuum container 232. The deflecting module 270 deflects the electron beam discharged from the cathode 236 to move the focus point onto the target surface 235*b*.

The X-ray tube device of Example 2 is formed in this manner.

The X-ray CT apparatus 1 according to the first embodiment configured as described above includes the X-ray tube device 10, the cooling unit 20, the X-ray detector 40, and the rotary gantry frame 6. The cooling unit 20 includes the circulation pump 22, the radiator 24, and the fan unit 25. The rotary gantry frame 6 includes the frame 7. The X-ray tube device 10, the circulation pump 22, the radiator 24, the fan unit 25, and the X-ray detector 40 are installed in the rotary gantry frame 6.

The distance from the rotation axis a1 to the fan unit 25 is longer than the distance from the rotation axis a1 to the radiator 24. The fan unit 25 discharges the air flowing around the radiator 24 to the outside of the rotary gantry frame 6 through the opening 7*a*.

The radiator 24 is not closely installed in the frame 7. The size of the opening 7*a* is not necessarily equal to the size of the radiator 24, but may be smaller than the size of the radiator 24. For this reason, it is possible to suppress a decrease of the mechanical strength of the frame 7. Since it is not necessary to reinforce the frame 7 by increasing a width or a thickness, it is possible to reduce the size and the weight of the apparatus.

As an operation time of the X-ray CT apparatus 1 increases, dust is deposited on the gap between the heat-radiating fins or the heat-radiating pipes of the radiator 24. Then, this makes the air difficult to pass through the radiator 24 and degrades cooling performance of the heat exchanger 23 and a cooling rate of the X-ray tube.

However, the windward side of the radiator 24 is exposed in the space of the inner wall side space of the frame 7. For this reason, it is possible to clean the radiator 24 from the inner wall side space of the frame 7 by removing only a part of the casing 2 to remove dust deposited on the radiator 24. Since the radiator 24 can be cleaned without removing the cooling unit 20 from the rotary gantry frame 6 or collectively removing the X-ray tube device 10 connected to the cooling unit 20, it is possible to reduce a time for the cleaning (maintenance) work.

Since overheating generated in the X-ray tube 13 can be prevented by maintaining the heat exchanger 23 without degrading performance, it is possible to prevent an electric discharge frequently generated in the X-ray tube 13. Therefore, it is possible to prevent a decrease of the product service life of the X-ray tube 13.

In this manner, it is possible to obtain the X-ray CT apparatus 1 capable of preventing degradation of a mechanical strength and performing cleaning without removing the radiator 24 from the rotary gantry frame 6.

Next, an X-ray CT apparatus according to a second embodiment will be described. In the second embodiment, other configurations are similar to those of the first embodiment described above. Therefore, like reference numerals denote like elements, and the description thereof will not be repeated. FIGS. 11 and 12 are front views illustrating a rotary gantry frame 6, and an X-ray tube device 10, a cooling unit 20 and an X-ray detector 40 mounted on the rotary gantry frame 6 of the X-ray CT apparatus 1 according to the second embodiment.

Referring to FIG. 11, the cooling unit 20 is not provided with the casing 50. The cooling unit 20 is provided with mounts 27 and 28. The mounts 27 and 28 are formed in a rectangular frame shape. One end of the mount 27 is installed in an inner wall of the frame 7. The mount 27 surrounds the opening 7a. A side peripheral portion of mount 28 is installed in the inner wall of the frame 7.

The circulation pump 22 is positioned inside the mount 28 and is installed in the mount 28. Therefore, the circulation pump 22 is indirectly installed and fixed to the inner wall of the frame 7.

The expansion mechanism 60 is positioned between the mount 28 and the rotation axis a1 and is placed on the mount 28. Therefore, the expansion mechanism 60 is indirectly installed and fixed to the inner wall of the frame 7.

A fringe portion of the radiator 24 is installed in the other end of the mount 27. Therefore, the radiator 24 is indirectly installed and fixed to the inner wall of the frame 7. Naturally, the windward side of the radiator 24 is exposed in the inner wall side space of the frame 7.

The fan unit 25 is directly installed in the frame 7. Here, the fan unit 25 is directly installed and fixed to opening 7a of the frame 7.

For this reason, the mount 27 is positioned between the radiator 24 and the fan unit 25, and also serves as a duct that guides the air flow around the radiator 24 to the fan unit 25.

The X-ray CT apparatus 1 according to the second embodiment configured in this manner is provided with the mount 27. For this reason, it is possible to form the X-ray CT apparatus 1 without providing the casing 50 of the first embodiment in which a design of the mechanical strength is difficult.

The X-ray CT apparatus 1 is provided with the mount 28. Since the expansion mechanism 60 can be placed on the mount 28, it is possible to design a compact cooling unit 20.

The size of the opening 7a is not necessarily equal to the size of the radiator 24, but may be smaller than the size of the radiator 24. For this reason, it is possible to suppress degradation of the mechanical strength of the frame 7. Since it is not necessary to reinforce the frame 7 by increasing a width or a thickness, it is possible to reduce a size and a weight of the apparatus.

The windward side of the radiator 24 is exposed in the inner wall side space of the frame 7. For this reason, it is possible to clean the radiator 24 from the inner wall side space of the frame 7 to remove dust deposited on the radiator 24 by removing only a part of the casing 2. Since the radiator 24 can be cleaned without removing the cooling unit 20 from the rotary gantry frame 6 or collectively removing the X-ray tube device 10 connected to the cooling unit 20, it is possible to reduce a time for a cleaning (maintenance) work.

Since overheating generated in the X-ray tube 13 can be prevented by performing maintenance without degrading performance of the heat exchanger 23, it is possible to prevent an electric discharge frequently generated in the X-ray tube 13. Therefore, it is possible to prevent a decrease of the product service life of the X-ray tube 13.

In this manner, it is possible to obtain the X-ray CT apparatus 1 capable of preventing degradation of a mechanical strength and performing cleaning without removing the radiator 24 from the rotary gantry frame 6.

Next, an X-ray CT apparatus according to a third embodiment will be described. In the third embodiment, other configurations are similar to those of the first embodiment described above. Therefore, like reference numerals denote like elements, and the description thereof will not be repeated. FIG. 12 is a front view illustrating a rotary gantry frame 6, and an X-ray tube device 10, a cooling unit 20 and an X-ray detector 40 mounted on the rotary gantry frame 6 of the X-ray CT apparatus 1 according to the third embodiment.

Referring to FIG. 12, the cooling unit 20 is not provided with the casing 50 described above. The cooling unit 20 is provided with a mount 29. The mount 29 includes a circumferential wall having a rectangular frame shape, a ceiling wall having a plate shape, and a pair of side walls having a plate shape positioned between the circumferential wall and the ceiling wall, integrated into a single body. The circumferential wall of the mount 29 is installed in an inner wall of the frame 7. The circumferential wall of the mount 29 surrounds the opening 7a.

The circulation pump 22 and the expansion mechanism 60 are positioned between the mount 29 and the rotation axis a1 and are placed on the ceiling wall of the mount 29. Therefore, the circulation pump 22 and the expansion mechanism 60 are indirectly installed and fixed to the inner wall of the frame 7.

A fringe portion of the radiator 24 is installed in the circumferential wall of the mount 29. Therefore, the radiator 24 is indirectly installed and fixed to the inner wall of the frame 7. In the inner wall side space of the frame 7, a pair of side walls of the mount 29 have a predetermined height in order to expose the windward side of the radiator 24. In other words, a pair of side walls of the mount 29 have a predetermined height such that the radiator 24 can be cleaned from a space between the radiator 24 and the ceiling wall of the mount 29. In addition, since the air is allowed to access the space between the radiator 24 and the ceiling wall of the mount 29, the air passing through the space between the radiator 24 and the ceiling wall of the mount 29 passes through the radiator 24.

The fan unit 25 is directly installed in the frame 7. Here, the fan unit 25 is directly installed and fixed to the opening 7a of the frame 7.

For this reason, the circumferential wall of the mount 29 is positioned between the radiator 24 and the fan unit 25 and also serves as a duct that guides the air flow around the radiator 24 to the fan unit 25.

The X-ray CT apparatus 1 according to the third embodiment configured in this manner is provided with the mount 29. For this reason, it is possible to form the X-ray CT apparatus 1 without providing the casing 50 of the first embodiment in which a design of the mechanical strength is difficult.

Since the circulation pump 22 and the expansion mechanism 60 can be placed on the ceiling wall of the mount 29, it is possible to design the cooling unit 20 in a compact manner.

The size of the opening 7a is not necessarily equal to the size of the radiator 24, but may be smaller than the size of the radiator 24. For this reason, it is possible to suppress degradation of the mechanical strength of the frame 7. Since it is not necessary to reinforce the frame 7 by increasing a width or a thickness, it is possible to reduce a size and a weight of the apparatus.

Since a pair of side walls of the mount 29 have a predetermined height, the windward side of the radiator 24 is exposed in the inner wall side space of the frame 7. The radiator 24 can be accessed from the space between the radiator 24 and the ceiling wall of the mount 29. For this reason, it is possible to clean the radiator 24 from the inner wall side space of the frame portion 7 to remove dust deposited on the radiator 24 by removing only a part of the casing 2. Since the radiator 24 can be cleaned without removing the cooling unit 20 from the rotary gantry frame 6 or collectively removing the X-ray tube device 10 connected to the cooling unit 20, it is possible to reduce a time for a cleaning (maintenance) work.

Since overheating generated in the X-ray tube 13 can be prevented by performing maintenance without degrading performance of the heat exchanger 23, it is possible to prevent an electric discharge frequently generated in the X-ray tube 13. Therefore, it is possible to prevent a decrease of the product service life of the X-ray tube 13.

In this manner, it is possible to obtain the X-ray CT apparatus 1 capable of preventing degradation of a mechanical strength and performing cleaning without removing the radiator 24 from the rotary gantry frame 6.

Next, an X-ray CT apparatus according to a fourth embodiment will be described. In the fourth embodiment, other configurations are similar to those of the first embodiment described above. Therefore, like reference numerals denote like elements, and the description thereof will not be repeated. FIG. 13 is a front view illustrating a rotary gantry frame 6, and an X-ray tube device 10, a cooling unit 20 and an X-ray detector 40 mounted on the rotary gantry frame 6 of the X-ray CT apparatus 1 according to the fourth embodiment.

Referring to FIG. 13, the cooling unit 20 is not provided with the casing 50 described above. The cooling unit 20 is provided with the mounts 28 and 29.

The mount 28 is formed in a rectangular frame shape. A side peripheral portion of the mount 28 is installed in the inner wall of the frame 7.

The circulation pump 22 is positioned inside the mount 28 and is installed in the mount 28. Therefore, the circulation pump 22 is indirectly installed and fixed to the inner wall of the frame 7.

The expansion mechanism 60 is positioned between the mount 28 and the rotation axis a1 and is placed on the mount 28. Therefore, the expansion mechanism 60 is indirectly installed and fixed to the inner wall of the frame portion 7.

The mount 29 includes a circumferential wall having a rectangular frame shape, a ceiling wall having a plate shape, and a pair of side walls having a plate shape positioned between the circumferential wall and the ceiling wall, integrated into a single body. The circumferential wall of the mount 29 is installed in an inner wall of the frame 7. The circumferential wall of the mount 29 surrounds the opening 7a.

The X-ray tube device 10 (housing 12) is positioned between the mount 29 and the rotation axis a1 and is placed on the ceiling wall of the mount 29. Therefore, the X-ray tube device 10 is indirectly installed and fixed to the inner wall of the frame 7.

A fringe of the radiator 24 is installed in the circumferential wall of the mount 29. Therefore, the radiator 24 is indirectly installed and fixed to the inner wall of the frame 7. In the inner wall side space of the frame 7, a pair of side walls of the mount 29 have a predetermined height in order to expose the windward side of the radiator 24. In other words, a pair of side walls of the mount 29 have a predetermined height such that the radiator 24 can be cleaned from a space between the radiator 24 and the ceiling wall of the mount 29. In addition, since the air is allowed to access the space between the radiator 24 and the ceiling wall of the mount 29, the air passing through the space between the radiator 24 and the ceiling wall of the mount 29 passes through the radiator 24.

The fan unit 25 is directly installed in the frame 7. Here, the fan unit 25 is directly installed and fixed to the opening 7a of the frame 7.

For this reason, the circumferential wall of the mount 29 is positioned between the radiator 24 and the fan unit 25 and also serves as a duct that guides the air flow around the radiator 24 to the fan unit 25.

The X-ray CT apparatus 1 according to the fourth embodiment configured in this manner is provided with the mount 29. For this reason, it is possible to form the X-ray CT apparatus 1 without providing the casing 50 of the first embodiment in which a design of the mechanical strength is difficult.

Since the expansion mechanism 60 is placed on the mount 28, and the X-ray tube device 10 (housing 12) can be placed on the ceiling wall of the mount 29, it is possible to design the cooling unit 20 in a compact manner.

The size of the opening 7a is not necessarily equal to the size of the radiator 24, but may be smaller than the size of the radiator 24. For this reason, it is possible to suppress degradation of the mechanical strength of the frame 7. Since it is not necessary to reinforce the frame 7 by increasing a width or a thickness, it is possible to reduce a size and a weight of the apparatus.

Since a pair of side walls of the mount 29 have a predetermined height, the windward side of the radiator 24 is exposed in the inner wall side space of the frame 7. The radiator 24 can be accessed from the space between the radiator 24 and the ceiling wall of the mount 29. For this reason, it is possible to clean the radiator 24 from the inner wall side space of the frame 7 to remove dust deposited on the radiator 24 by removing only a part of the casing 2. Since the radiator 24 can be cleaned without removing the cooling unit 20 from the rotary gantry frame 6 or collectively removing the X-ray tube device 10 connected to the cooling unit 20, it is possible to reduce a time for a cleaning (maintenance) work.

Since overheating generated in the X-ray tube 13 can be prevented by performing maintenance without degrading performance of the heat exchanger 23, it is possible to prevent an electric discharge frequently generated in the X-ray tube 13. Therefore, it is possible to prevent a decrease of the product service life of the X-ray tube 13.

In this manner, it is possible to obtain the X-ray CT apparatus 1 capable of preventing degradation of a mechanical strength and performing cleaning without removing the radiator 24 from the rotary gantry frame 6.

Figure 15:
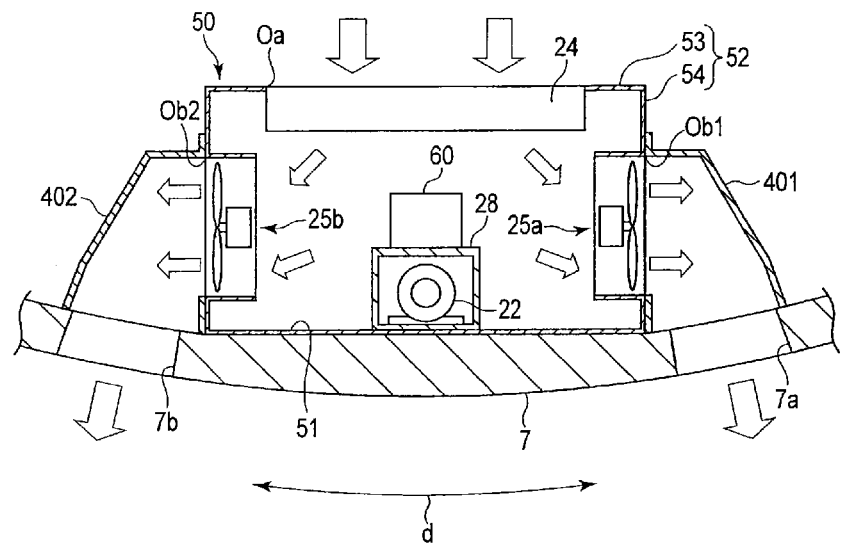
FIG. 15 is a partially enlarged schematic diagram illustrating the X-ray CT apparatus according to the fifth embodiment, including a frame, a circulation pump, a radiator, a fan unit, a mount, a casing, an expansion mechanism, and a duct.

Next, an X-ray CT apparatus according to a fifth embodiment will be described. In the fifth embodiment, other configurations are similar to those of the first embodiment described above. Therefore, like reference numerals denote like elements, and the description thereof will not be repeated. FIG. 14 is a front view illustrating a rotary gantry frame 6, and an X-ray tube device 10, a cooling unit 20 and an X-ray detector 40 mounted on the rotary gantry frame 6 of the X-ray CT apparatus 1 according to the fifth embodiment. FIG. 15 is a partially enlarged schematic diagram illustrating the X-ray CT apparatus 1 according to the fifth embodiment, including a frame 7, a circulation pump 22, a radiator 24, fan units 25a and 25b, a mount 28, a casing 50, an expansion mechanism 60, and ducts 401 and 402.

Referring to FIGS. 14 and 15, the casing 50 has a bottom wall 51 and a lid 52, and is installed in the rotary gantry frame. The bottom wall 51 faces the inner wall of the frame 7. The lid 52 includes a first ventilation port Oa and second ventilation ports Ob1 and Ob2. The lid 52 has a ceiling wall 53 and a circumferential wall 54. The ceiling wall 53 includes the first ventilation port Oa and faces the bottom wall 51 with an interval. The circumferential wall 54 includes the second ventilation ports Ob1 and Ob2 and is formed in a frame shape. The circumferential wall 54 has one end closed by the ceiling wall 53 and the other end closed by the bottom wall 51. The second ventilation port Ob1 and the second ventilation port Ob2 face each other in a rotational direction d of the rotary gantry frame 6.

In this embodiment, the bottom wall 51 and the ceiling wall 53 are formed in a rectangular plate shape, and the circumferential wall 54 is formed in a rectangular frame shape. The casing 50 is formed in an air-tight manner except for the first and second ventilation ports Oa, Ob1, and Ob2.

The mount 28, the circulation pump 22, and the expansion mechanism 60 are housed in the casing 50. The mount 28 is formed in a rectangular frame shape. A side peripheral portion of the mount 28 is installed in the bottom wall 51. The circulation pump 22 is positioned inside the mount 28 and is installed in the mount 28. In this embodiment, a rotation axis of a motor of the circulation pump 22 is parallel with the rotation axis a1 of the rotary gantry frame 6. The expansion mechanism 60 is positioned between the mount 28 and the rotation axis a1 and is placed on the mount 28. Therefore, the expansion mechanism 60 is indirectly installed in the casing 50.

The radiator 24, and the fan units 25a and 25b are housed and unitized in the casing 50. The radiator 24 is installed in the casing 50 (ceiling wall 53). The windward side of the radiator 24 is exposed to the outside of the casing 50 through the first ventilation port Oa.

The fan units 25a and 25b are installed in the casing 50 (circumferential wall 54). The fan unit 25a is positioned to face the second ventilation port Ob1. The fan unit 25b is positioned to face the second ventilation port Ob2. The fan units 25a and 25b can generate an air flow passing through the radiator 24. The fan unit 25a introduces the air flowing through the radiator 24 into the inside of the casing 50 through the first ventilation port Oa and discharges the air inside the casing 50 to the outside of the casing 50 through the second ventilation port Ob1. The fan unit 25b introduces the air flowing around the radiator 24 into the inside of the casing 50 through the first ventilation port Oa, and discharges the air inside the casing 50 to the outside of the casing 50 through the second ventilation port Ob2.

The frame 7 includes openings 7a and 7b deviating from the position facing the bottom wall 51 of the casing 50.

One end of the duct 401 is installed in the circumferential wall 54 while the duct 401 surrounds a periphery of the second ventilation port Ob1 and communicates with the second ventilation port Ob1. The other end of the duct 401 is installed in the frame 7 while the duct 401 surrounds a periphery of the opening 7a and communicates with the opening 7a. The duct 401 guides, to the opening 7a, the air discharged to the outside of the casing 50 through the second ventilation port Ob1 and discharges the guided air to the outside of the rotary gantry frame 6 (frame 7).

One end of the duct 402 is installed in the circumferential wall 54 while the duct 402 surrounds a periphery of the second ventilation port Ob2 and communicates with the second ventilation port Ob2. The other end of the duct 402 is installed in the frame 7 while the duct 402 surrounds a periphery of the opening 7b and communicates with the opening 7b. The duct 402 guides, to the opening 7b, the air discharged to the outside of the casing 50 through the second ventilation port Ob2 and discharges the guided air to the outside of the rotary gantry frame 6 (frame 7).

In this embodiment, the ducts 401 and 402 are integrated with the frame 7. In order to improve the air guide effect, the duct 401 and the frame 7 are preferably connected to each other in an air-tight manner. Similarly, the duct 402 and the frame 7 are preferably connected to each other in an air-tight manner. Furthermore, one end of the duct 401 and one end of the duct 402 are preferably installed in the circumferential wall 54 in an air-tight manner.

In the X-ray CT apparatus 1 according to the fifth embodiment configured in this manner, the fan units 25a and 25b discharge the air flowing around the radiator 24 into the outside of the casing 50 through the second ventilation ports Ob1 and Ob2, and discharge the air to the outside of the rotary gantry frame 6 through the openings 7a and 7b.

The radiator 24 is not closely installed in the frame 7. The size of the opening 7a or 7b is not necessarily equal to the size of the radiator 24, but may be smaller than the size of the radiator 24. For this reason, it is possible to suppress a decrease of the mechanical strength of the frame 7. Since it is not necessary to reinforce the frame 7 by increasing a width or a thickness, it is possible to reduce the size and the weight of the apparatus.

As an operation time of the X-ray CT apparatus 1 increases, dust is easily deposited on the gap between the heat-radiating fins or the heat-radiating pipes of the radiator 24. Then, this makes the air difficult to pass through the radiator 24, and degrades cooling performance of the heat exchanger 23 and a cooling rate of the X-ray tube 13.

However, the windward side of the radiator 24 is exposed in the space of the inner wall side space of the frame 7. For this reason, it is possible to clean the radiator 24 from the inner wall side space of the frame 7 by removing only a part of the casing 2 to remove dust deposited on the radiator 24. Since the radiator 24 can be cleaned without removing the cooling unit 20 from the rotary gantry frame 6 or collectively removing the X-ray tube device 10 connected to the cooling unit 20, it is possible to reduce a time for the cleaning (maintenance) work.

Since overheating generated in the X-ray tube 13 can be prevented by performing maintenance without degrading performance of the heat exchanger 23, it is possible to prevent an electric discharge frequently generated in the X-ray tube 13. Therefore, it is possible to prevent a decrease of the product service life of the X-ray tube 13.

The radiator 24 is installed in the ceiling wall 53, and the fan units 25a and 25b are installed in the circumferential wall 54. For this reason, it is possible to place the circulation pump 22 and the expansion mechanism 60 on the bottom wall 51 without increasing a size of the casing 50. Since the circulation pump 22, the radiator 24, the fan units 25a and 25b, and the expansion mechanism 60 can be installed in the rotary gantry frame 6 in a compact manner, it is possible to improve space efficiency in the inner wall side of the frame 7.

Here, even when the circulation pump 22 and the expansion mechanism 60 are housed in the casing 50, they do not adversely affect the air flow around the radiator 24. Therefore, it is possible to preserve cooling performance of the heat exchanger 23.

The rotation axis of the motor of the circulation pump 22 is parallel with the rotation axis a1 of the rotary gantry frame 6. Since a gyroscopic moment is not exerted to the rotation axis of the motor of the circulation pump 22, it is possible to lengthen a product service life of the circulation pump 22.

As described above, it is possible to obtain the X-ray CT apparatus 1 capable of preventing a decrease of the mechanical strength and performing cleaning without removing the radiator 24 from the rotary gantry frame 6. In addition, it is possible to obtain the X-ray CT apparatus 1 having excellent space efficiency in the inner wall side of the frame 7.

Figure 16:
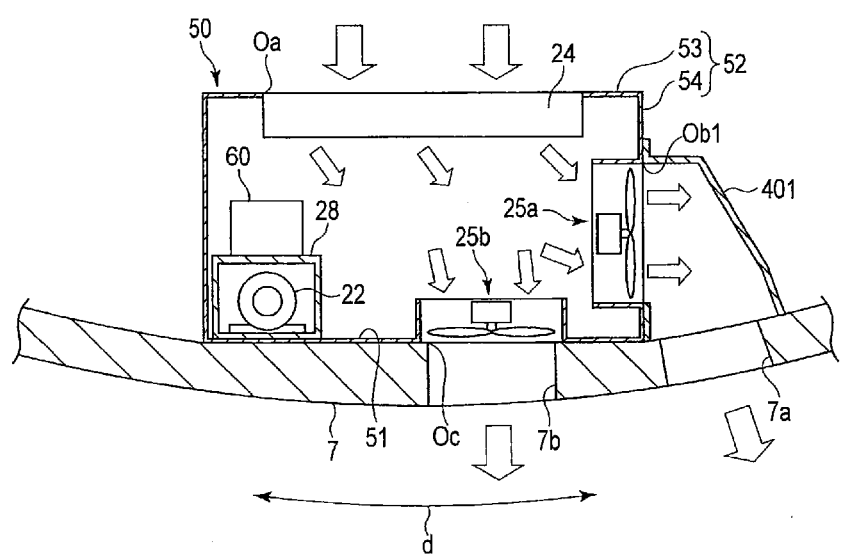
FIG. 16 is a partially enlarged schematic diagram illustrating an X-ray CT apparatus according to a sixth embodiment, including a frame, a circulation pump, a radiator, a fan unit, a mount, a casing, an expansion mechanism, and a duct.

Next, an X-ray CT apparatus according to a sixth embodiment will be described. In the sixth embodiment, other configurations are similar to those of the fifth embodiment described above. Therefore, like reference numerals denote like elements, and the description thereof will not be repeated. FIG. 16 is a partially enlarged schematic diagram illustrating the X-ray CT apparatus 1 according to the sixth embodiment, including a frame 7, a circulation pump 22, a radiator 24, fan units 25a and 25b, a mount 28, a casing 50, an expansion mechanism 60, and a duct 401.

Referring to FIG. 16, the X-ray CT apparatus 1 is formed without a duct 402. The circumferential wall 54 does not have the second ventilation port Ob2. The bottom wall 51 includes a third ventilation port Oc. The fan unit 25b is installed in the casing 50 (bottom wall 51) and is positioned to face the third ventilation port Oc. The opening 7b of the frame 7 faces the third ventilation port Oc.

The mount 28 is installed in the bottom wall 51 deviating from the opening 7b. The fan unit 25b introduces the air flowing through the radiator 24 into the inside of the casing 50 through the first ventilation port Oa, and discharges the air inside the casing 50 to the outside of the rotary gantry frame 6 through the third ventilation port Oc and the opening 7b. In order to effectively discharge the air to the outside of the rotary gantry frame 6, the third ventilation port Oc and the opening 7b preferably communicate with each other in an air-tight manner.

In the X-ray CT apparatus 1 according to the sixth embodiment configured in this manner, when there is a margin in the area of the bottom wall 51, the circulation pump 22 and the expansion mechanism 60 may be placed on the bottom wall 51, and the third ventilation port Oc may be formed in the bottom wall 51. In addition, the fan unit 25b may be installed in the bottom wall 51.

In this case, similar to the fifth embodiment, it is possible to place the circulation pump 22 and the expansion mechanism 60 on the bottom wall 51 without increasing a size of the casing 50. Since the circulation pump 22, the radiator 24, the fan units 25a and 25b, and the expansion mechanism 60 can be installed in the rotary gantry frame 6 in a compact manner, it is possible to improve space efficiency in the inner wall side of the frame 7.

In addition, the same effects as those of the fifth embodiment can be obtained.

As described above, it is possible to obtain the X-ray CT apparatus 1 capable of preventing a decrease of the mechanical strength and performing cleaning without removing the radiator 24 from the rotary gantry frame 6. In addition, it is possible to obtain the X-ray CT apparatus 1 having excellent space efficiency in the inner wall side of the frame 7.

Next, an X-ray CT apparatus according to a seventh embodiment will be described. In the seventh embodiment, other configurations are similar to those of the fifth embodiment described above. Therefore, like reference numerals denote like elements as in the fifth embodiment, and the description thereof will not be repeated. FIG. 17 is a partially enlarged schematic diagram illustrating an X-ray CT apparatus 1 according to the seventh embodiment, including a frame 7, a circulation pump 22, a radiator 24, fan units 25a and 25b, a mount 28, a casing 50, and an expansion mechanism 60. FIG. 18 is a cross-sectional view illustrating a part of the X-ray CT apparatus 1 taken along the line XVIII-XVIII of FIG. 17.

Referring to FIGS. 17 and 18, second ventilation ports Ob1 and Ob2 are opened in parallel with the rotation axis a1 of the rotary gantry frame 6. The second ventilation ports Ob1 and Ob2 are formed side by side in a side wall of the circumferential wall 54. The duct 401 communicates with the second ventilation port Ob1 and the opening 7a. Although not illustrated in the drawings, other ducts (402) also communicate with the second ventilation port Ob2 and the opening (7b).

Each of the fan units 25a and 25b includes an axial flow fan. The rotation axis of the axial flow fan is in parallel with the rotation axis a1 of the rotary gantry frame.

In the X-ray CT apparatus 1 according to the seventh embodiment configured in this manner, each of the fan units 25a and 25b includes an axial flow fan, and the rotation axis of the axial flow fan is parallel with the rotation axis a1. Since a gyroscopic moment is not exerted to the rotation axis of the motor of the axial flow fan, it is possible to lengthen a product service life of the fan units 25a and 25b.

In addition, the same effects as those of the fifth embodiment can be obtained.

As described above, it is possible to obtain the X-ray CT apparatus 1 capable of preventing a decrease of the mechanical strength and performing cleaning without removing the radiator 24 from the rotary gantry frame 6. In addition, it is possible to obtain the X-ray CT apparatus 1 having excellent space efficiency in the inner wall side of the frame 7.

Next, an X-ray CT apparatus according to an eighth embodiment will be described. In the eighth embodiment, other configurations are similar to those of the seventh embodiment described above. Therefore, like reference numerals denote like elements as in the fifth embodiment, and the description thereof will not be repeated. FIG. 19 is a partially enlarged schematic diagram illustrating the X-ray CT apparatus 1 according to the eighth embodiment, including a frame 7, a circulation pump 22, a radiator 24, fan units 25a, 25b, 25c and 25d, a mount 28, a casing 50, and an expansion mechanism 60. FIG. 20 is a cross-sectional view illustrating a part of the X-ray CT apparatus 1 taken along a line XX-XX of FIG. 19.

Referring to FIGS. 19 and 20, the bottom wall 51 includes third ventilation ports Oc1 and Oc2. The heat exchanger 23 further includes fan units 25c and 25d. The fan unit 25c is installed in the casing 50 (bottom wall 51) and is positioned to face the third ventilation port Oc1. The fan unit 25d is installed in the casing 50 (bottom wall 51) and is positioned to face the third ventilation port Oc2. The frame 7 further includes openings 7c and 7d. The opening 7c of the frame 7 faces the third ventilation port Oc1. The opening 7d of the frame 7 faces the third ventilation port Oc2.

The mount 28 is installed in the bottom wall 51 deviating from the openings 7c and 7d.

The fan unit 25c introduces the air flowing through the radiator 24 into the inside of the casing 50 through the first ventilation port Oa, and discharges the air inside the casing 50 into the outside of the rotary gantry frame 6 through the third ventilation port Oc1 and the opening 7c.

The fan unit 25d introduces the air flowing through the radiator 24 into the inside of the casing 50 through the first ventilation port Oa, and discharges the air inside the casing 50 into the outside of the rotary gantry frame 6 through the third ventilation port Oc2 and the opening 7d.

In order to effectively discharge the air to the outside of the rotary gantry frame 6, it is preferable that the third ventilation port Oc1 and the opening 7c communicate with each other, and the third ventilation port Oc2 and the opening 7d communicate with each other in an air-tight manner.

In the X-ray CT apparatus 1 according to the eighth embodiment configured in this manner, when there is a margin in the area of the bottom wall 51, the circulation pump 22 and the expansion mechanism 60 may be placed on the bottom wall 51, the third ventilation ports Oc1 and Oc2 may be formed in the bottom wall 51, and the fan units 25c and 27d may be installed in the bottom wall 51.

In this case, similar to the seventh embodiment, it is possible to place the circulation pump 22 and the expansion mechanism 60 on the bottom wall 51 without increasing a size of the casing 50. Since the circulation pump 22, the radiator 24, the fan units 25a, 25b, 25c and 25d, and the expansion mechanism 60 are installed in the rotary gantry frame 6 in a compact manner, it is possible to improve space efficiency in the inner wall side of the frame 7. In addition, it is possible to further improve cooling performance of the heat exchanger 23.

In addition, the same effects as those of the seventh embodiment can be obtained.

As described above, it is possible to obtain the X-ray CT apparatus 1 capable of preventing a decrease of the mechanical strength, and performing cleaning without removing the radiator 24 from the rotary gantry frame 6. In addition, it is possible to obtain the X-ray CT apparatus 1 having excellent space efficiency in the inner wall side of the frame 7.

Figure 21:
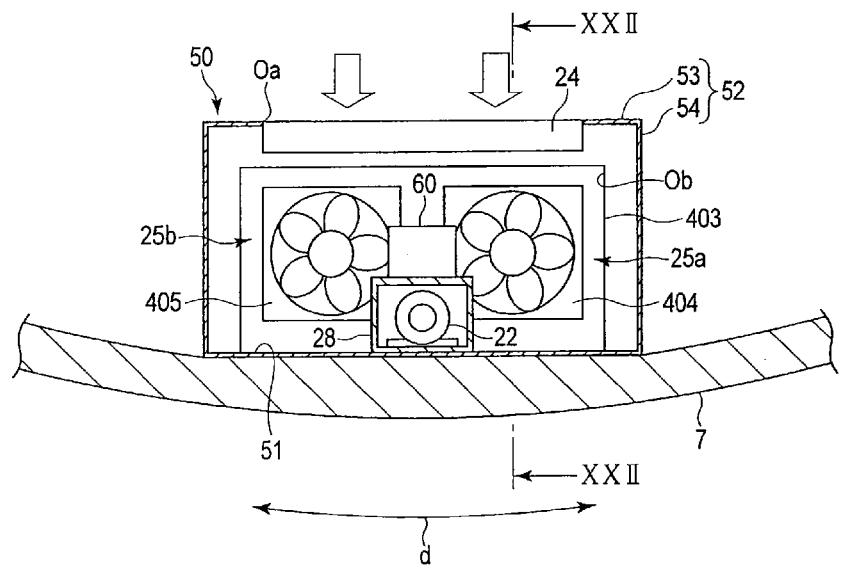
FIG. 21 is a partially enlarged schematic diagram illustrating an X-ray CT apparatus according to a ninth embodiment, including a frame, a circulation pump, a radiator, a fan unit, a mount, a casing, an expansion mechanism, and a duct.
Figure 22:
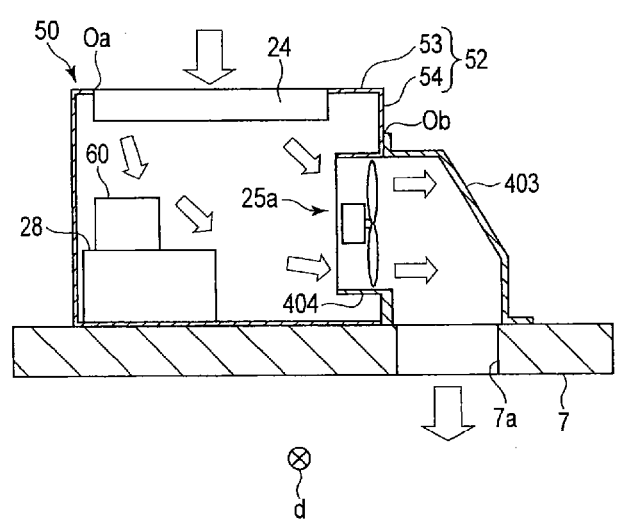
FIG. 22 is a partial cross-sectional view illustrating the X-ray CT apparatus taken along a line XXII-XXII of FIG. 21.

Next, an X-ray CT apparatus according to a ninth embodiment will be described. In the ninth embodiment, other configurations are similar to those of the seventh embodiment described above. Therefore, like reference numerals denote like elements as in the fifth embodiment, and the description thereof will not be repeated. FIG. 21 is a partially enlarged schematic diagram illustrating the X-ray CT apparatus 1 according to the ninth embodiment, including a frame 7, a circulation pump 22, a radiator 24, fan units 25a and 25b, a mount 28, a casing 50, an expansion mechanism 60, and a duct 403. FIG. 22 is a cross-sectional view illustrating a part of the X-ray CT apparatus 1 taken along a line XXII-XXII of FIG. 21.

Referring to FIGS. 21 and 22, a second ventilation port Ob is formed in the circumferential wall 54 instead of the second ventilation ports Ob1 and Ob2.

One end of the duct 403 is installed in the circumferential wall 54 while the duct 403 surrounds a periphery of the second ventilation port Ob, and communicates with the second ventilation port Ob. The other end of the duct 403 is installed in the frame 7 to surround a periphery of the opening 7a, and communicates with the opening 7a. The duct 403 guides, to the opening 7a, the air discharged to the outside of the casing 50 through the second ventilation port Ob, and discharges the air to the outside of the rotary gantry frame 6 (frame 7).

In this embodiment, the duct 403 is integrated with the frame 7. In order to improve cooling performance of the heat exchanger 23, the duct 403 and the circumferential wall 54 are preferably connected to each other in an air-tight manner.

Each of the fan units 25a and 25b includes an axial flow fan. The rotation axis of the axial flow fan is in parallel with the rotation axis a1 of the rotary gantry frame. The fan units 25a and 25b are installed in the duct 403. The outer wall 404 of the fan unit 25a and the outer wall 405 of the fan unit 25b are formed in a part of the duct 403.

In the X-ray CT apparatus 1 according to the ninth embodiment configured in this manner, each of the fan units 25a and 25b is installed in the duct 403. The fan units 25a and 25b are not necessarily unitized with the casing 50, the radiator 24, and the like. Even in this case, it is possible to obtain the same effects as those of the seventh embodiment.

As described above, it is possible to obtain the X-ray CT apparatus 1 capable of preventing a decrease of the mechanical strength and performing cleaning without removing the radiator 24 from the rotary gantry frame 6. In addition, it is possible to obtain the X-ray CT apparatus 1 having excellent space efficiency in the inner wall side of the frame 7.

Figure 28:
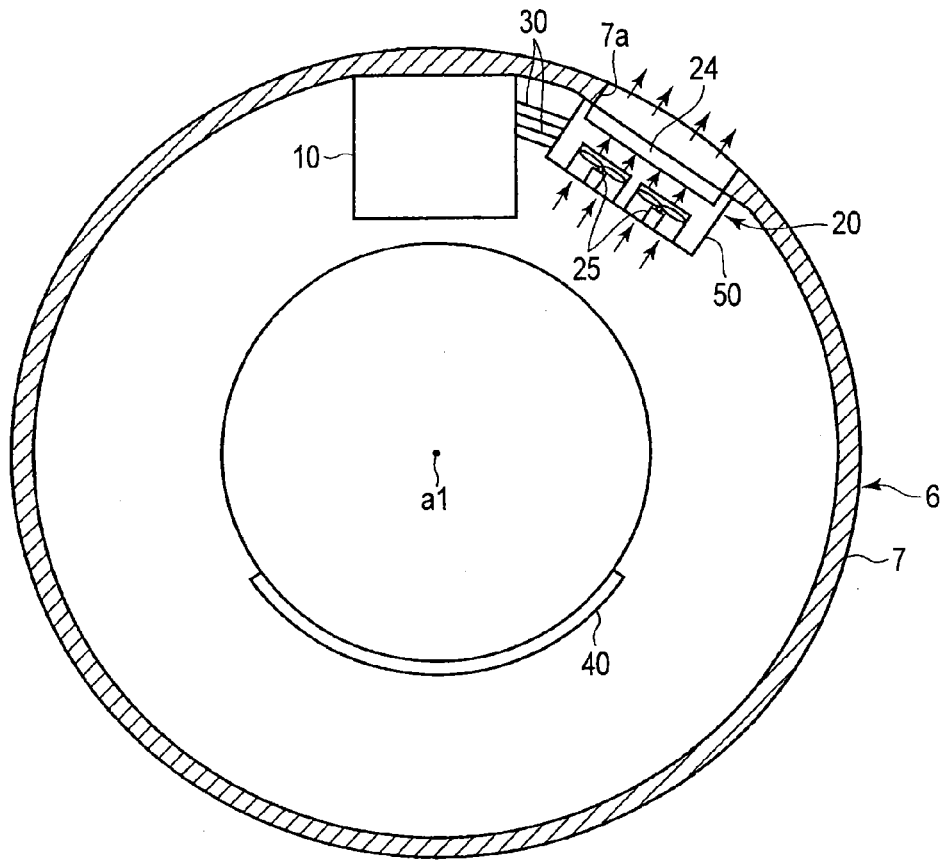
FIG. 28 is a front view illustrating a rotary gantry frame, and an X-ray tube device, a cooling unit and an X-ray detector mounted on the rotary gantry frame in a comparative example of the X-ray CT apparatus.

Next, a comparative example of the X-ray CT apparatus according the first to fourth embodiments will be described. It is noted that the X-ray CT apparatus of this comparative example is also a comparative example of the X-ray CT apparatus according to the fifth to ninth embodiments. FIG. 28 is a front view illustrating a rotary gantry frame 6, and the X-ray tube device 10, the cooling unit 20 and the X-ray detector 40 mounted on the rotary gantry frame 6 of the X-ray CT apparatus of the comparative example.

Referring to FIG. 28, the radiator 24 is positioned between the opening 7a and the fan unit 25. The radiator 24 is closely installed in the frame 7. A distance from the rotation axis a1 to the fan unit 25 is shorter than a distance from the rotation axis a1 to the radiator 24. A size of the opening 7a is approximately equal to that of the radiator 24.

In the comparative example of the X-ray CT apparatus configured in this manner, the radiator 24 is closely installed in the frame 7. Therefore, it is necessary to make a size of the opening 7a approximately equal to that of the radiator 24. As the size of the opening 7a increases, a mechanical strength of the frame 7 decreases. In this case, it is necessary to reinforce the frame 7 by increasing a width or a thickness. Therefore, it is difficult to reduce a size and a weight of the apparatus.

When it is difficult to remove the cooling unit 20 from the rotary gantry frame 6 or separate the cooling unit 20 and the X-ray tube device 10 for cleaning the radiator 24, it is necessary to collectively remove the X-ray tube device 10 connected to the cooling unit 20. Therefore, it is difficult to reduce a time for a cleaning (maintenance) work.

It is noted that this invention is not limited to the embodiments described above, but may be embodied by modifying or changing elements without departing from the spirit and scope thereof in an implementation stage. In addition, various changes or modifications may be possible by appropriately combining a plurality of elements disclosed in the aforementioned embodiments. For example, some element may be removed from overall elements described in the embodiments. Furthermore, elements of other embodiments may also be appropriately combined.

For example, the expansion mechanism 60 may be provided separately from the cooling unit 20 if it is installed in the circulation path 30.

Figure 23:
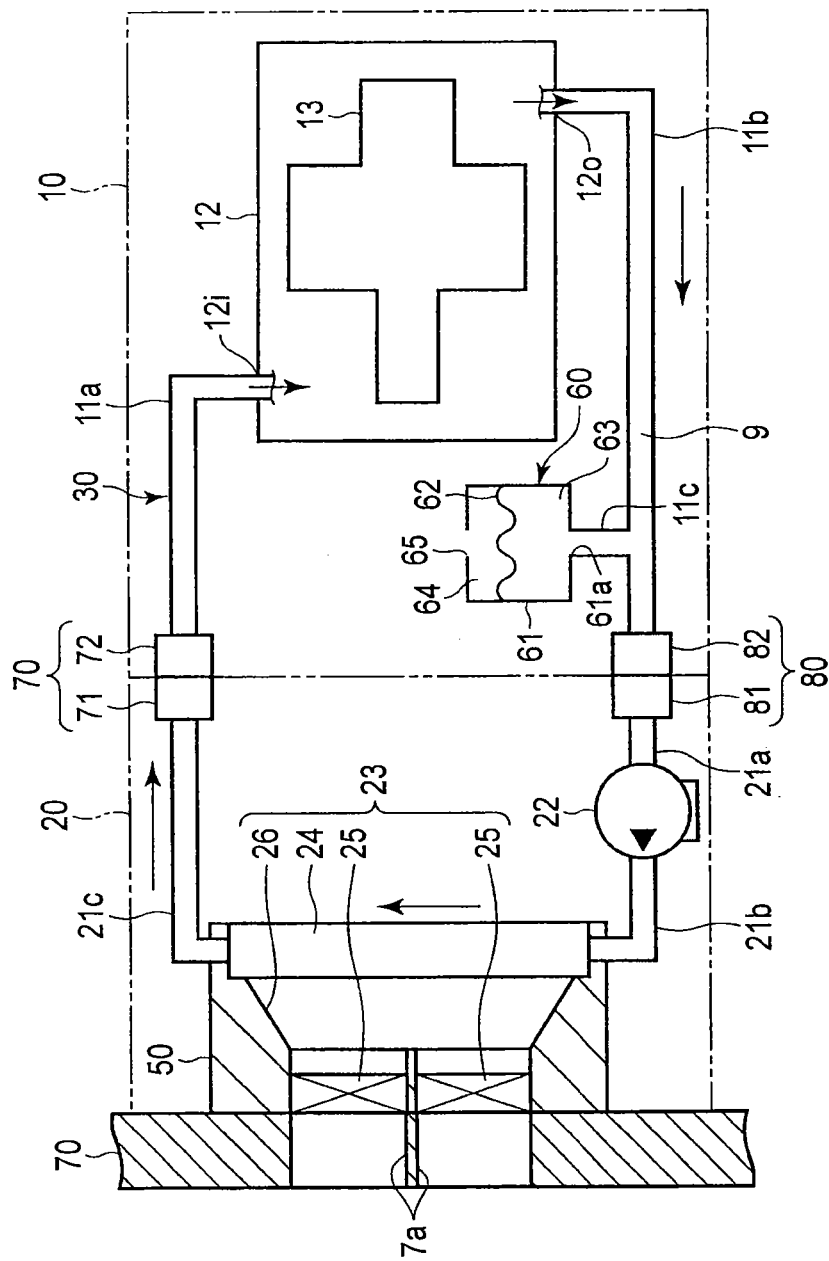
FIG. 23 is a conceptual diagram illustrating a modification of the X-ray CT apparatus, including the X-ray tube device and the cooling unit.

As illustrated in FIG. 23, the expansion mechanism 60 may be provided in the X-ray tube device 10. One end of the conduit 11c is installed in the conduit 11b in an air-tight manner. The opening 61a of the expansion mechanism 60 communicates with the conduit 11c in an air-tight manner.

Figure 24:
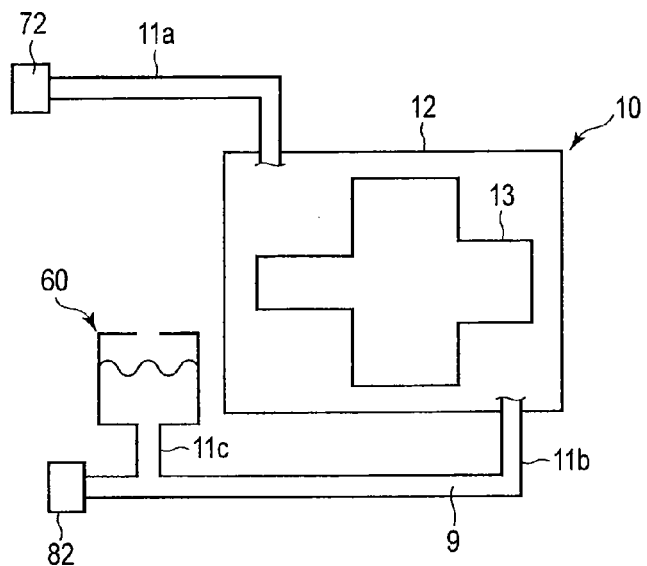
FIG. 24 is a schematic diagram illustrating a disconnected state of the X-ray tube device of FIG. 23.

FIG. 24 is a schematic diagram illustrating a disconnected state of the X-ray tube device 10 of FIG. 23.

Referring to FIG. 24, the X-ray tube device 10 having the disconnected state is provided with the expansion mechanism 60. For this reason, it is possible to prevent an external leakage of the liquid (coolant 9) and intrusion of the air in the X-ray tube device 10 having the disconnected state without adding something to the X-ray tube device 10.

In the cooling unit 20 having the disconnected state, it is difficult to absorb a volume change of the coolant 9. In this regard, a functionality of absorbing a volume change of the coolant 9 may be provided in the conduits 21a, 21b, and 21c if the conduits 21a, 21b, and 21c are formed of a hose. However, in some cases, it is difficult to sufficiently absorb a volume change of the coolant 9 only using the conduits 21a, 21b, and 21c. In this case, an expansion mechanism is preferably installed in the cooling unit 20 having the disconnected state.

Figure 25:
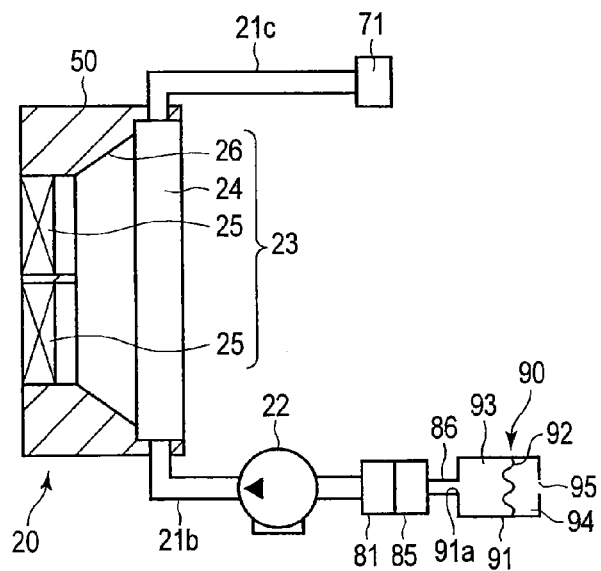
FIG. 25 is a schematic diagram illustrating a disconnected state of the cooling unit of FIG. 23.

FIG. 25 is a schematic diagram illustrating a disconnected state of the cooling unit 20 of FIG. 23.

Referring to FIG. 25, an expansion mechanism 90 is installed in the cooling unit 20. The expansion mechanism 90 is installed in the cooling unit 20 using a socket 85 and a conduit 86 connected to each other in an air-tight and liquid-tight manner. A plug 81 and the socket 85 form a coupler as a removable coupling and are connected in an air-tight and liquid-tight manner in a connected state. An opening 91a communicates with the conduit 86 in an air-tight manner.

As a result, in the cooling unit 20 having the disconnected state, it is possible to prevent an external leakage of the liquid (coolant 9) and intrusion of the air.

As illustrated in FIG. 26, the X-ray CT apparatus 1 may further comprises a pressure detector 301, a pressure control unit 302, a pressure regulating mechanism 303, and a conduit 304. The pressure detector 301 (pressure sensor) is installed in the vessel 61 in an air-tight manner. The pressure detector 301 detects a pressure (gas pressure) of the second area 64. The pressure detector 301 transmits information about the detected pressure to the pressure control unit 302. The pressure control unit 302 controls driving of the pressure regulating mechanism 303 based on the information about the pressure.

The pressure regulating mechanism 303 communicates with the ventilation port 65 through the conduit 304 in an air-tight manner. Needless to say, it is noted that the second area 64 is not opened to the atmospheric air in this example. The pressure regulating mechanism 303 can control the gas pressure in the second area 64.

When the pressure regulating mechanism 303 serves as a compressing mechanism, the gas pressure of the second area 64 can be regulated to a positive pressure higher than the atmospheric pressure. When the pressure regulating mechanism 303 serves as a decompressing mechanism, the gas pressure of the second area 64 can be regulated to a negative pressure lower than the atmospheric pressure.

In a state where the temperature of the coolant 9 is sufficiently low, such as an initial state immediately after the X-ray tube device 10 starts to operate, the pressure regulating mechanism 303 regulates the pressure of the second area 64 to a negative pressure to lower a boiling point of the coolant 9 in order to increase a heat flow velocity. Furthermore, as the X-ray tube device 10 is continuously operated, and a temperature of the heat transfer surface of the X-ray tube 13 increases, the temperature of the coolant 9 also increases. For this reason, as the temperature of the coolant 9 increases, the pressure regulating mechanism 303 regulates the pressure of the second area 64 to the atmospheric pressure and increases the boiling point of the coolant 9. In addition, the pressure regulating mechanism 303 regulates the pressure of the second area 64 to the positive pressure and further increases the boiling point of the coolant 9. As a result, it is possible to transfer the boiling heat discharged from the heat transfer surface of the X-ray tube 13 to the coolant 9. In addition, since it is possible to obtain a sufficient heat flow velocity without generating a burnout, a continuous input can be performed under a constant X-ray tube input power.

In this case, the X-ray CT apparatus 1 is preferably provided with a temperature detector for detecting a temperature of the coolant 9. For example, the temperature detector may detect a temperature of the coolant 9 in the upstream side of the heat transfer surface of the X-ray tube 13. The X-ray CT apparatus 1 may further comprises another temperature detector. Another temperature detector may detect a temperature of the coolant 9 in the downstream side of the heat transfer surface of the X-ray tube 13.

As illustrated in FIG. 27, the second area 64 of the expansion mechanism 60 may not be opened to the atmospheric air, but may be hermetically sealed. The second area 64 is filled with a gas, and a pressure thereof is regulated to a positive pressure. Since it is possible to increase a boiling point of the coolant 9, it is possible to prevent a burnout.

An aqueous coolant, an insulating oil, and the like may be employed as the coolant 9. The aqueous coolant may contain an antifreeze fluid such as a glycol water.

A centrifugal pump or a gear pump may be employed as the circulation pump 22.

When the X-ray tube device 10 and the cooling unit 20 are not separated, the X-ray CT apparatus 1 may be formed without couplers 70 and 80.

The circulation pump 22, the radiator 24, the fan unit 25, and the expansion mechanism 60 may be housed and unitized in the casing 50.

The expansion mechanism 60 may be directly or indirectly installed in the rotary gantry frame 6 independently from the X-ray tube device 10 (housing 12), the circulation pump 22, the radiator 24, and the fan unit 25.

The circulation pump 22, the radiator 24, and the fan unit 25 may be housed and unitized in the casing 50.

The X-ray tube device 10 (housing 12), the circulation pump 22, the radiator 24, the fan unit 25, and the expansion mechanism 60 may be directly or indirectly installed in the rotary gantry frame 6 independently from each other.

The expansion mechanism 60 may be installed in the outer surface of the X-ray tube device 10 (housing 12).

Although the radiator 24 has a flat plate shape and is arranged substantially in parallel with the inner wall of the frame 7, various modifications may be possible. The radiator 24 may be formed in any shape. For example, the radiator 24 may be formed in a stack type or may be arranged to incline against the inner wall of the frame 7.

The radiator 24 may be installed to cover the ventilation port provided in the circumferential wall 54 of the casing 50.

When a rotation speed of the rotary gantry frame 6 exceeds 3 rps, it is preferable that the fan unit 25 be directly installed in the opening 7a of the rotary gantry frame 6 as described in the second to fourth embodiments in order to reliably obtain a mechanical strength. In addition, it is preferable that each of the radiator 24, the expansion mechanism 60, and the circulation pump 22 communicating with the circulation path be installed in a dedicated mount fixed on the rotary gantry frame 6. As a modification of the second to fourth embodiments, at least one of the circulation pump 22, the duct 26, and the expansion mechanism 90 may be housed in a single casing along with the radiator 24, and this casing may be installed in the rotary gantry frame 6 to position immediately over the fan unit.

The ducts 401, 402, and 403 may be provided as necessary.

The heat exchanger 23 may have a plurality of radiators 24. For example, a plurality of radiators 24 may be stacked. In this meaning, the radiator will be referred to as a radiator unit in the following description.

The casing 50 may be shaped to increase the surface area of the radiator unit 24. The casing 50 may have a ceiling wall protruding in a roof shape including the ventilation port. The ceiling wall is formed in a mountain shape. In this case, the radiator unit 24 is housed in the casing 50 such that the windward side is exposed to the outside of the casing 50 through the ventilation port.

In the X-ray CT apparatus described above, the ventilation port is provided in the frame 7, and the air flow passing through the radiator unit 24 is discharged to the outside of the rotary gantry frame 6 (in the side opposite to the rotational center axis a1) through the ventilation port. However, even when the ventilation port is not provided in the frame 7, the heated air does not remain inside the casing 2 of the X-ray CT apparatus if the air flow passing through the radiator unit 24 and the air flow discharged from the inside of the casing of the cooling unit to the outside of the casing of the cooling unit through the ventilation port of the casing of the cooling unit are directed to recede from the rotational center axis a1. Therefore, it is possible to prevent an increase of the internal atmospheric temperature of the casing 2 or degradation of the cooling performance of the cooling unit or sensitivity of the X-ray detector.

The embodiments of the invention may be applied to various types of X-ray CT apparatuses or other X-ray diagnosis apparatuses without limiting to the X-ray CT apparatus described above.

Next, a CT apparatus according to the tenth embodiment will be described with reference to the accompanying drawings.

Figure 30:
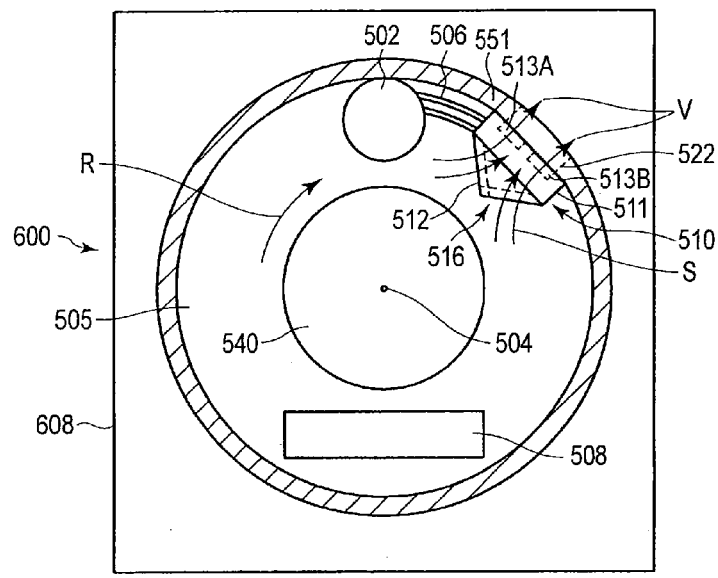
FIG. 30 is a cross-sectional view schematically illustrating a structure of the rotor in the X-ray CT apparatus of FIG. 29.

FIG. 29 illustrates an exterior of a computer tomographic (CT) apparatus according to the tenth embodiment, and FIG. 30 schematically illustrates an interior structure of the CT apparatus of FIG. 29. This CT apparatus is provided with a gantry 600. The gantry 600 includes a rotor 505 rotating around the rotational center axis 504, a support structure (not illustrated) that rotatably supports the rotor 5, and a casing 608 that surrounds the rotor 505. In the center of the gantry 600, a gantry aperture 540 is provided as a shooting area, where an examinee couch 620 accesses. When the examinee is photographically shot, the couch 620 advances to the inside of the gantry aperture 540 so that the examinee is disposed in the shooting area.

The rotor 505 is formed as a ring-like frame. An X-ray generator 502 having a collimator (not illustrate) for generating an X-ray in a fan beam shape is fixed to the rotor 505. In addition, an X-ray detector 508 arranged to face the X-ray generator 502 by interposing the shooting area of the gantry aperture 540 for detecting an X-ray in a fan beam shape is also fixed to the rotor 505. Furthermore, a cooler 510 for cooling the X-ray generator 502 described below in detail is fixed to the rotor 505.

In this CT apparatus, the rotor 505 is rotated, and an X-ray fan beam is irradiated onto an examinee (not illustrated) from the X-ray generator 502 while a couch 620 where an examinee (not illustrated) is laid accesses the gantry aperture 540. Then, the transmitting X-ray is detected by the X-ray detector 508. As the rotor 505 is rotated, the X-ray fan beam is irradiated from various directions around the examinee, so that the X-ray is detected by the X-ray detector 508 from a plurality of portions of the examinee. The detection signal from the X-ray detector 508 is output the outside of the rotor 505 and is supplied to an image restructuring module (not illustrated). The image restructuring module processes this output signal to compute transmissivity in various portions of the examinee so as to restructure a tomographic image of the examinee.

The cooler 510 is connected to the X-ray generator 502 through a pipe 506 where a coolant is circulated. The heat generated in the X-ray generator 502 is transferred to the coolant and is supplied to the cooler 510 through the pipe 506 for discharging the heat. The coolant cooled in the cooler 510 is supplied to the X-ray generator 502 through the pipe 506 to absorb heat.

FIGS. 31, 32, 33, and 34 illustrate the cooler 510 of FIGS. 29 and 30 according to the tenth embodiment.

A base 531 is provided in a cooler fixing surface 552 of a cooler mount 551 on a frame of the rotor 505 where the cooler 510 is placed and fixed. A plurality of exhaust ports 517A and 517B communicating with the ventilation portion 522 formed in a frame of the rotor 505 are provided in the base 531. In addition, a plurality of posts 518A and 518B are erected on the post fixation surface 532 of the base 531 adjacently to the outer circumference of the base 531 and are fixed to the post fixation surface 532 using a coupling member such as a screw. In addition, a cooler casing cover 511 fixed to the base 531 is provided around a plurality of posts 518A and 518B, so that a space surrounded by the cooler casing cover 511 is defined as a ventilation space.

The cooler 510 is provided with a plurality of cooling fans 513A and 513B as a plurality of fan units. The cooling fans 513A and 513B are arranged to surround the cooler casing cover 511 on the exhaust ports 517A and 517B. In addition, the radiator unit 512 is fixed to a front face of the ventilation space in the rotational center axis 504 side where the cooling fans 513A and 513B ventilates the air so as to cover the opening of the cooler casing cover 511.

The cooler casing 611 includes the cooler casing cover 511, surrounds internal components of the cooler 510, and defines an internal space of the cooler 510 and a ventilation space on the base 531. In addition, the cooler casing 611 also defines an air intake 516 where the radiator unit 512 is arranged.

The support structure 560 is fixed to the post fixation surface 532 of the base 531 using a plurality of posts 518A and 518B in order to support the radiator unit 512. The support structure 560 has a fixation seat 520 for installing and fixing the radiator unit 512 and a plurality of posts 518A and 518B erected on the post fixation surface 532. More specifically, the fixation seat 520 is fixed to fixation seat fixing surfaces 681A and 681B of a plurality of posts 518A and 518B, and a plurality radiators 519A and 519B of the radiator unit 512 are placed and fixed to the fixation seat 520. Fluid paths of the radiators 519A and 519B are connected to each other in parallel. Here, the fixation seat 520 includes frame structures 523A and 523B having a triangular roof shape such that apex portions of a plurality of radiators 519A and 519B are directed to the rotational center axis 4 side. More specifically, the fixation seat 520 includes the installation portions (plate-like members) 521A and 521B, and plate-like reinforcing members 522A and 522B fixed to the installation portions 521A and 521B. In the reinforcing members 522A and 522B (in the drawings, illustrated as, for example, an L-shaped cross section), cross section adjacent to a rear surface (surface directed to the ventilation space) of the installation portions 521A and 521B has an L-shape or a T-shape, as enlargedly indicated across a cross section A-A. One end of the installation portions 521A and 521B and one end of the reinforcing members 522A and 522B of the fixation seat 520 are installed and fixed to the fixation seat fixing surfaces 681A and 681B provided in the rotational center axis 504 side of a plurality of posts 518A and 518B using a fixing member such as a screw. In addition, the other end of the installation portions 521A and 521B and the other end of the reinforcing members 522A and 522B abut on each other to form a roof-like apex portion and are installed and fixed using a fixing member such as a screw. By placing and fixing a plurality of radiators 519A and 519B to the fixation seat 520 having such a structure, the radiators 519A and 519B are also arranged in a roof shape in this manner. Therefore, a plurality of radiators 519A and 519B have air intakes 516A and 516B in a front face of the rotational center axis 4 side thereof, and the air intakes 516A and 516B constitute an intake duct 516 of the cooler 510.

Figure 31:
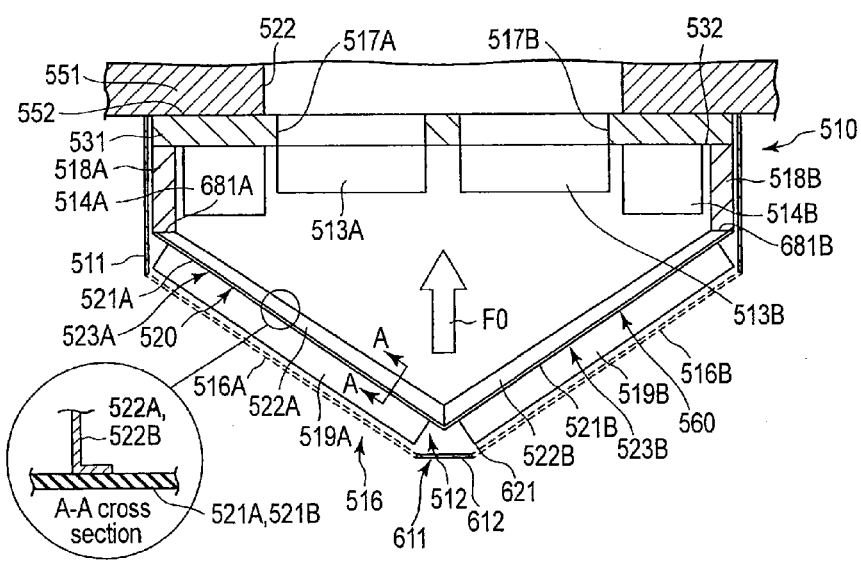
FIG. 31 is a cross-sectional view schematically illustrating a structure of the cooler according to the tenth embodiment illustrated in FIG. 30.

Pumps 514A and 514B of FIG. 31 as a circulation pump are connected to the radiator unit 512. A pipe 506 is connected to the pumps 514A and 514B. Therefore, the coolant heated by the X-ray generator 502 is supplied to the pumps 514A and 514B through the pipe 506 and is then supplied from the pumps 514A and 514B to the radiator unit 512. Here, when the radiator unit 512 includes a plurality of radiators 519A and 519B whose fluid paths are connected to each other in parallel, the coolant is supplied from the bases of the pumps 514A and 514B to the radiators 519A and 519B in parallel. In addition, the coolant cooled by the radiator unit 512 passes through the radiators 519A and 519B and joins together. Then, the coolant is supplied from the radiator unit 512 to the X-ray generator 502 through the pipe 506.

Here, the radiators 519A and 519B include a heat-radiating pipe (not illustrated) where the coolant flows to discharge the heat to the atmospheric air and a heat-radiating fin (not illustrated) connected to the heat-radiating pipe for increasing a heat-radiating area.

The cooling fans 513A and 513B are surrounded by the cooler casing cover 511 and the radiator unit 512. As the cooling fans 513A and 513B are operated, the intake air flow S is introduced into the radiator unit 512 from the outside of the cooler 510 through the air intakes 516A and 516B, passes through the radiator unit 512, and flows to the ventilation space. The intake air flow S is discharged as an exhaust air flow V to the outside of the ventilation space through the ventilation portion 522 by the cooling fans 513A and 513B. Therefore, in the radiator unit 512, the heated coolant is cooled by the intake air flow S. Heat transfer is generated such that the intake air flow S is heated by the coolant. As a result, the heat of the X-ray generator 502 is discharged to the outside of the cooler 510.

Figure 32:
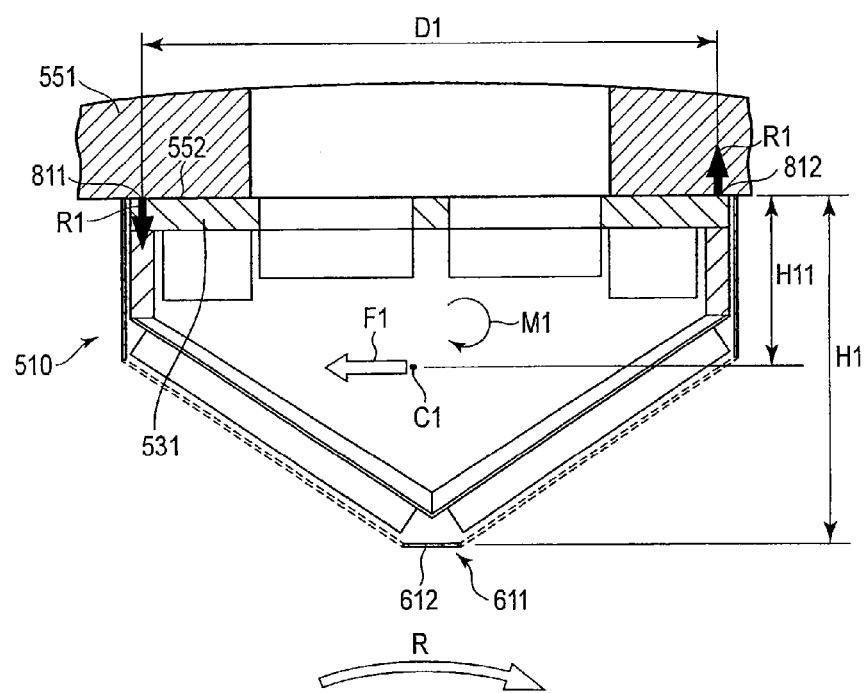
FIG. 32 is a cross-sectional view schematically illustrating a characteristic of the cooler according to the tenth embodiment illustrated in FIG. 30.

A characteristic of the tenth embodiment will be described with reference to FIG. 32.

In the base 531, a first base fixing portion 811 for fixing the base 531 to the cooler fixing surface 552 is provided adjacently to one side in the upstream side of the base 531 in the rotational direction R of the rotor 5, and a second base fixing portion 812 for fixing the base 531 to the cooler fixing surface 552 is provided adjacently to one side of the downstream side of the base 531 in the rotational direction R of the rotor 5. A height H1 of the apex portion 612 of the cooler casing 611 from the cooler fixing surface 552 is set to be smaller than a distance D1 between the first base fixing portion 811 and the second base fixing portion 812.

A characteristic of the tenth embodiment will be further described with reference to FIG. 33.

In the support structure 560, a first support structure fixing portion 901 for fixing the support structure 560 to the post fixation surface 532 is provided in a plurality of posts 518A located in the upstream side of the support structure 560 in the rotational direction R of the rotor 505, and a second support structure fixing portion 902 for fixing the support structure 560 to the post fixation surface 532 is provided in a plurality of posts 518B in the downstream side of the support structure 560 in the rotational direction R of the rotor 505. A height H2 of the apex portion 621 of the radiator unit 512 from the post fixation surface 532 is set to be smaller than a distance D2 between the first support structure fixing portion 901 and the second support structure fixing portion 902.

Figure 34:
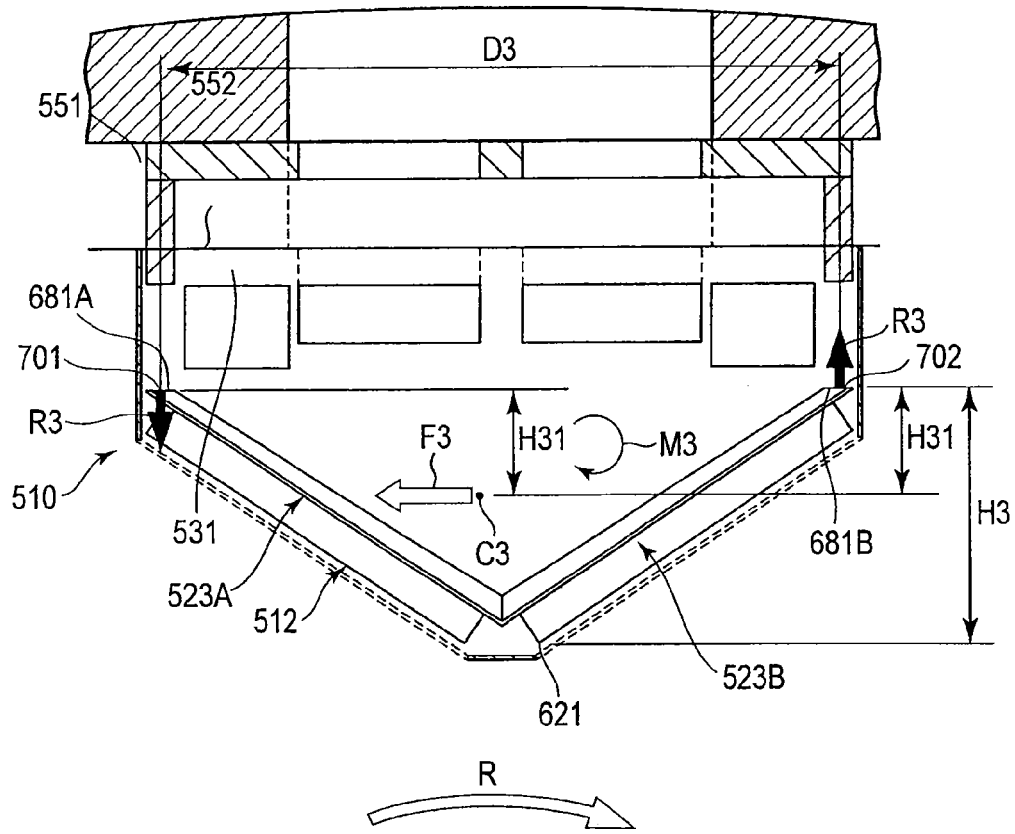
FIG. 34 is a cross-sectional view schematically illustrating a characteristic of the cooler according to the tenth embodiment illustrated in FIG. 30.

A characteristic of the tenth embodiment will be further described with reference to FIG. 34.

In the fixation seat 520, a first fixation seat fixing portion 701 for fixing the fixation seat 520 to the fixation seat fixing surfaces 681A of a plurality of posts 518A is provided in the frame structure 523A in the upstream side of the fixation seat 520 in the rotational direction R of the rotor 505, and a second fixation seat fixing portion 702 for fixing the fixation seat 520 to the fixation seat fixing surfaces 681B of a plurality of posts 518B is provided in the frame structure 523B in the downstream side of the fixation seat 520 in the rotational direction R of the rotor 505. A height H3 of the apex portion 621 of the radiator unit 512 from the fixation seat fixing surface 681A and 681B is set to be smaller than a distance D3 between the first fixation seat fixing portion 701 and the second fixation seat fixing portion 702.

As the rotor 505 is rotated in the rotational direction R, a centrifugal force F0 is applied to the cooler 510 toward the outer side of the radial direction of the rotor 505. For example, as the rotor 505 is rotated, a centrifugal force F0 of 32G or higher is applied to the radiator unit 512. Here, the centrifugal force F0 applied to the radiator unit 512 is loaded on the roof-shaped fixation seat 520 included in the support structure of the radiator unit 512. In addition, the fixation seat 520 is provided with a plate-like portion (having L-shaped or T-shaped one side portion with a width along the centrifugal force F0) of the reinforcing members 522A and 522B in a direction where the centrifugal force F0 is applied. Therefore, the fixation seat 520 can sufficiently endure the load of the centrifugal force F0. Since the fixation seat 520 is not a simple plate shape, deformation of the fixation seat 520 is prevented. In addition, the load applied to the fixation seat 520 is transmitted to the fixing portions 701 and 702 of the fixation seat 520 along a roof direction, that is, along an elongating direction of the installation portion (plate-like member) 521A and 521B and is transmitted to the posts 518A and 518B having high rigidity and to the base 531 having sufficient rigidity.

As the rotor 505 is acceleratingly rotated as indicated by the rotational direction R, such as when rotation of the rotor starts, an inertia force F1 is applied to the cooler 510 in a direction opposite to the rotational direction R of the rotor 505. Here, the cooler 510 is fixed to the cooler fixing surface 552, and the inertia force F1 is applied in the position of the height H11 of the center of mass C1 of the cooler 510 from the cooler fixing surface 552. Therefore, the inertia force F1 generates a moment M1 (a product of F1 and H11) to the fixing portion of the cooler 510 (that is, the first base fixing portion 811 and the second base fixing portion 812). The moment M1 generates a pair of reactive forces R1 applied to the first and second base fixing portions 811 and 812, and is balanced by the moment (a product of R1 and D1) caused by a resultant force of a pair of reactive forces R1. The reactive force R1 is applied to a fixing member such as a screw of the fixing portion as a load. The moment M1 is applied to separate the cooler 510 from the cooler fixing surface 552, so that a fixing member such as a screw of the first and second base fixing portions 811 and 812 may be damaged. Therefore, it is necessary to suppress the moment M1.

Here, according to this embodiment, the height H1 of the apex portion 612 of the cooler casing 611 from the cooler fixing surface 552 is set to be smaller than the distance D1 between the first and second base fixing portions 811 and 812. Therefore, the height H11 (smaller than H1) of the center of mass C1 of the cooler 510 from the cooler fixing surface 552 is also suppressed to be smaller than the distance D1 between the first and second base fixing portions 811 and 812. As a result, a magnitude of a pair of reactive forces R1 applied to the first and second base fixing portions 811 and 812 is reduced to be smaller than the inertia force F1. Therefore, when rotation of the rotor is accelerated, a load applied to a fixing member such as a screw of the fixing portion (first and second base fixing portions 811 and 812) of the cooler 510 is suppressed to be small. Therefore, it is possible to prevent damage.

As the rotor 505 is acceleratingly rotated as indicated by the rotational direction R, such as when rotation of the rotor starts, an inertia force F2 is applied to the support structure 560 and the radiator unit 512 fixed to the support structure 560 in a direction opposite to the rotational direction R of the rotor 505. Here, the support structure 560 is fixed to the post fixation surface 532, and the inertia force F2 is applied in the position of the height H21 of the center of mass C2 of a combination of the support structure 560 and the radiator unit 512 from the post fixation surface 532. Therefore, the inertia force F2 generates a moment M2 (a product of F2 and H21) against the fixing portion (first and second support structure fixing portions 901 and 902) of the support structure 560. The moment M2 generates a pair of reactive forces R2 applied to the first and second support structure fixing portions 901 and 902, and is balanced by a moment (a product of R2 and D2) generated by a resultant force of a pair of reactive forces R2. The reactive force R2 is applied to a fixing member such as a screw of the fixing portion as a load. The moment M2 is applied to separate the support structure 560 from the post fixation surface 532, so that a fixing member such as a screw in the first and second support structure fixing portions 901 and 902 may be damaged. Therefore, it is necessary to suppress the moment M2.

Here, according to this embodiment, the height H2 of the apex portion 621 of the radiator unit 512 from the post fixation surface 532 is set to be smaller than the distance D2 between the first and second support structure fixing portions 901 and 902. Therefore, the height H21 (smaller than H2) of the center of mass C2 of a combination of the support structure 560 and the radiator unit 512 from the post fixation surface 532 is also suppressed to be smaller than the distance D2 between the first and second support structure fixing portions 901 and 902. As a result, a magnitude of a pair of reactive forces R2 applied to the first and second support structure fixing portions 901 and 902 is reduced to be smaller than the inertia force F2. Therefore, when rotation of the rotor is accelerated, load applied to a fixing member such as a screw of the fixing portion (first and second support structure fixing portions 901 and 902) of the support structure 560 is suppressed to be small. Therefore, it is possible to prevent damage.

As the rotor 505 is acceleratingly rotated as indicated by the rotational direction R, such as when rotation of the rotor starts, an inertia force F3 is applied to the fixation seat 520 and the radiator unit 512 fixed to the fixation seat 520 in a direction opposite to the rotational direction R of the rotor 505. Here, the fixation seat 520 is fixed to the fixation seat fixing surfaces 681A and 681B, and the inertia force F3 is applied in the position of the height H31 of the center of mass C3 of a combination of the fixation seat 520 and the radiator unit 512 from the fixation seat fixing surfaces 681A and 681B. Therefore, the inertia force F3 generates a moment M3 (a product of F3 and H31) against the fixing portion (first and second fixation seat fixing portions 701 and 702) of the fixation seat 520. The moment M3 generates a pair of reactive forces R3 applied to the first and second fixation seat fixing portions 701 and 702, and is balanced by a moment (a product of R3 and D3) generated by a resultant force of a pair of reactive forces R3. The reactive force R3 is applied to a fixing member such as a screw of the fixing portion as a load. The moment M3 is applied to separate the fixation seat 520 from the fixation seat fixing surfaces 681A and 681B, so that a fixing member such as a screw in the first and second fixation seat fixing portions 701 and 702 may be damaged. Therefore, it is necessary to suppress the moment M3.

Here, according to this embodiment, the height H3 of the apex portion 621 of the radiator unit 512 from the fixation seat fixing surfaces 681A and 681B is set to be smaller than the distance D3 between the first and second fixation seat fixing portions 701 and 702. Therefore, the height H31 (smaller than H3) of the center of mass C3 of a combination of the fixation seat 520 and the radiator unit 512 from the fixation seat fixing surfaces 681A and 681B is also suppressed to be smaller than the distance D3 between the first and second fixation seat fixing portions 701 and 702. As a result, a magnitude of a pair of reactive forces R3 applied to the first and second fixation seat fixing portions 701 and 702 is reduced to be smaller than the inertia force F3. Therefore, when rotation of the rotor is accelerated, a load applied to a fixing member such as a screw of the fixing portion (first and second fixation seat fixing portions 701 and 702) of the fixation seat 520 is suppressed to be small. Therefore, it is possible to prevent damage.

A power supply of the X-ray generator 502 is provided in the gantry 600 outside the rotor 505 using a slip ring (not illustrated) and the like. Similarly, a power supply (not illustrate) of the cooling fans 513A and 513B and the pumps 514A and 514B may be provided on the rotor 505 or may be provided in the gantry 600 outside the rotor 505 as in the power supply of the X-ray generator 502.

As described above, since the radiator unit 512 is supported by the support structure having improved rigidity, deformation is not generated even when the centrifugal force F0 generated by rotation of the rotor is applied to the cooler. Therefore, a possibility of breakdown of components such as a heat-radiating pipe is reduced, and a tolerance for the centrifugal force is improved. In addition, since the radiator unit 512 is coupled to the base 531 using a plurality of posts 518a and 518b, it is possible to reliably support the radiator unit 512 by distributing the centrifugal force. Furthermore, a weight can be reduced in a portion where a load of the component such as the radiator unit 512 of the cooler 510 is not applied, for example, a portion where the centrifugal force is not applied such as the cooler casing cover 511.

Since the base 531 is fixed to the rotor, deformation of the base is prevented, and a possibility of breakdown of components is reduced even when a load caused by the centrifugal forces of the pumps 514A and 514B, the cooling fans 513A and 513B, and the power supply (not illustrated) is applied. As a result, it is possible to improve a tolerance of the cooler.

Moreover, even when the inertia forces F1, F2, and F3 generated by accelerating rotation of the rotor are applied to the cooler, the height of the center of mass C1 of the cooler from the cooler fixing surface 552, the height of the center of mass C2 of a combination of the support structure 560 and the radiator unit 512 from the post fixation surface 532, and the height of the center of mass C3 of a combination of the fixation seat 520 and the radiator unit 512 from the fixation seat fixing surfaces 681A and 681B are suppressed to be small. Therefore, the reactive force R1 applied to the fixing portion is reduced to be equal to or smaller than the inertia force F1, the reactive force R2 is reduced to be equal to or smaller than the inertia force F2, and the reactive force R3 is reduced to be equal to or smaller than the inertia force F3. Accordingly, a load applied to a fixing member such as a screw of the fixing portion is suppressed to be small, and it is possible to prevent damage. As a result, it is possible to improve a tolerance of the cooler.

In this manner, according to the tenth embodiment, it is possible to reliably obtain a tolerance against a centrifugal force and an inertia force caused by rotation of the rotor of the cooler whose size increases in order to respond to a high cooling capability.

As described above, according to the aforementioned embodiments, it is possible to implement a cooler having an improved tolerance against the centrifugal force and the inertia force caused by rotation of the rotor of the CT apparatus.

While an embodiment of the invention has been described, the embodiment is just for illustrative purposes and is not intended to limit the scope of the invention. Instead, the invention may be embodied in many other forms, and various deletions or modifications may be possible without departing from the scope and spirit of the invention. Such embodiments and modifications are intended to encompass the scope and spirit of the invention as set forth in the claims and equivalents thereof.

What is claimed is:

1. An X-ray computed tomography apparatus comprising:
   an X-ray tube device comprising a housing, and an X-ray tube housed in the housing, the X-ray tube including a cathode configured to discharge an electron beam, an anode target configured to discharge an X-ray by receiving the electron beam, and a vacuum envelope which stores the cathode and the anode target;
   a coolant where at least a part of heat generated in the X-ray tube is transferred;
   a circulation path where the coolant is circulated;
   a circulation pump installed in the circulation path to circulate the coolant;
   a radiator unit installed in the circulation path to externally discharge the heat of the coolant;
   a fan unit configured to generate an air flow passing through the radiator unit;
   an X-ray detector configured to detect the X-ray;
   a rotary gantry frame including a ring-shaped frame portion rotating with respect to a rotation axis, the X-ray tube device, the circulation pump, the radiator unit, the fan unit, and the X-ray detector being installed in the rotary gantry frame; and
   an expansion mechanism installed in the circulation path to absorb a volume change caused by a temperature change of the coolant,
   wherein a windward side of the radiator unit is exposed in an inner wall side space of the frame portion.

2. The X-ray computed tomography apparatus according to claim 1, wherein
   the housing, the radiator unit, the circulation pump and the expansion mechanism connected to form the circulation path are separable into a pair of channels using a pair of removable couplings.

3. An X-ray computed tomography apparatus comprising:
   an X-ray tube device comprising a housing, and an X-ray tube housed in the housing, the X-ray tube including a cathode configured to discharge an electron beam, an anode target configured to discharge an X-ray by receiving the electron beam, and a vacuum envelope which stores the cathode and the anode target;
   a coolant where at least a part of heat generated in the X-ray tube is transferred;
   a circulation path where the coolant is circulated;
   a circulation pump installed in the circulation path to circulate the coolant;
   a radiator unit installed in the circulation path to externally discharge the heat of the coolant;
   a fan unit configured to generate an air flow passing through the radiator unit;
   an X-ray detector configured to detect the X-ray;
   a rotary gantry frame including a ring-shaped frame portion rotating with respect to a rotation axis, the X-ray tube device, the circulation pump, the radiator unit, the fan unit, and the X-ray detector being installed in the rotary gantry frame; and
   a casing installed in the rotary gantry frame, the casing including a bottom wall facing an inner wall of the frame portion and a lid including first and second ventilation ports,
   wherein
   a windward side of the radiator unit is exposed in an inner wall side space of the frame portion,
   the radiator unit is housed in the casing such that the windward side is exposed to an outer side of the casing through the first ventilation port, and
   the fan unit is configured to introduce the air passing through the radiator into the casing through the first ventilation port, and discharge the air inside the casing to an outer side of the casing through the second ventilation port.

4. The X-ray computed tomography apparatus according to claim 3, wherein
   the lid comprises
   a ceiling wall which comprises the first ventilation port and faces the bottom wall with an interval, and
   a circumferential wall which includes the second ventilation port and is formed in a frame shape while one end of the circumferential wall is closed in the ceiling wall, and the other end of the circumferential wall is closed in the bottom wall.

5. The X-ray computed tomography apparatus according to claim 3, further comprising:
   a duct,
   wherein the frame portion includes an opening deviating from a position facing the bottom wall of the casing, and
   the duct guides, to the opening, the air discharged to the outside of the casing through the second ventilation port.

6. The X-ray computed tomography apparatus according to claim 3, wherein
   the circulation pump is housed in the casing.

7. The X-ray computed tomography apparatus according to claim 6, further comprising:

an expansion mechanism installed in the circulation path and housed in the casing to absorb a volume change caused by a temperature change of the coolant.

8. The X-ray computed tomography apparatus according to claim 3, further comprising:
another fan unit,
wherein the bottom wall includes a third ventilation port,
the frame portion includes an opening facing the third ventilation port, and
the another fan unit is configured to introduce the air passing through the radiator unit into the casing through the first ventilation port and discharge the air inside the casing to an outer side of the rotary gantry frame through the third ventilation port and the opening.

9. An X-ray computed tomography apparatus comprising:
an X-ray tube device comprising a housing, and an X-ray tube housed in the housing, the X-ray tube including a cathode configured to discharge an electron beam, an anode target configured to discharge an X-ray by receiving the electron beam, and a vacuum envelope which stores the cathode and the anode target;
a coolant where at least a part of heat generated in the X-ray tube is transferred;
a circulation path where the coolant is circulated;
a circulation pump installed in the circulation path to circulate the coolant;
a radiator unit installed in the circulation path to externally discharge the heat of the coolant;
a fan unit configured to generate an air flow passing through the radiator unit;
an X-ray detector configured to detect the X-ray; and
a rotary gantry frame including a ring-shaped frame portion rotating with respect to a rotation axis, the X-ray tube device, the circulation pump, the radiator unit, the fan unit, and the X-ray detector being installed in the rotary gantry frame,
wherein
a windward side of the radiator unit is exposed in an inner wall side space of the frame portion, and
a rotation axis of a motor of the circulation pump is parallel with a rotation axis of the rotary gantry frame.

10. A method of maintaining an X-ray computed tomography apparatus, comprising:
preparing the X-ray computed tomography apparatus comprising an X-ray tube device comprising a housing, and an X-ray tube housed in the housing, the X-ray tube including a cathode configured to discharge an electron beam, an anode target configured to discharge an X-ray by receiving the electron beam, and a vacuum envelope which stores the cathode and the anode target, a coolant where at least a part of heat generated in the X-ray tube is transferred, a circulation path where the coolant is circulated, a circulation pump installed in the circulation path to circulate the coolant, a radiator unit installed in the circulation path to externally discharge the heat of the coolant, a fan unit configured to generate an air flow passing through the radiator unit, an X-ray detector configured to detect the X-ray, a rotary gantry frame including a ring-shaped frame portion rotating with respect to a rotation axis, the X-ray tube device, the circulation pump, the radiator unit, the fan unit, and the X-ray detector being installed in the rotary gantry frame, and an expansion mechanism installed in the circulation path to absorb a volume change caused by a temperature change of the coolant, a windward side of the radiator unit being exposed in an inner wall side space of the frame portion;

dividing the housing, the radiator unit, the circulation pump, and the expansion mechanism connected to form the circulation path into a pair of channels using a pair of removable couplings; and
installing another expansion mechanism in a channel that does not include the expansion mechanism using the removable coupling.

11. A cooler mounted on a rotor to cool an X-ray generator that rotates around a rotational center axis along with the rotor, comprising:
a base which is fixed to a cooler fixing surface of the rotor and includes an exhaust port communicating with a ventilation portion provided in the rotor;
a first base fixing portion configured to fix the base to the cooler fixing surface and provided adjacently to one side in an upstream side of the base in a rotational direction of the rotor;
a second base fixing portion configured to fix the base to the cooler fixing surface and provided adjacently to one side in a downstream side of the base in a rotational direction of the rotor;
a radiator unit configured to discharge heat generated in the X-ray generator to an external atmosphere and connected to the X-ray generator through a pipe;
a circulation pump fixedly arranged on the base to circulate a coolant through the pipe between the X-ray generator and the radiator unit;
a casing which is configured to define a ventilation space on the base and an intake duct where the radiator unit is arranged;
a fan unit which is fixedly arranged in the base on the ventilation portion, and is configured to introduce air from an outer side of the casing to the ventilation space through the radiator unit provided in the intake duct and discharge air from the ventilation space through the exhaust port and the ventilation portion; and
a support structure fixed to the base that supports the radiator unit such that the radiator unit is arranged to protrude in a roof shape toward the rotational center axis side,
wherein a height of an apex portion of the casing from the cooler fixing surface is smaller than a distance between the first and second base fixing portions.

12. The cooler according to claim 11, wherein
the support structure includes a plurality of posts erected on a post fixation surface of the base, and a fixation seat fixedly installed in fixation seat fixing surfaces of a plurality of the posts,
the fixation seat includes a frame structure configured such that the fixation seat protrudes in a roof shape toward the rotational center axis, and
the radiator unit is fixedly installed in the frame structure.

13. The cooler according to claim 12, further comprising:
a first support structure fixing portion configured to fix the support structure to the post fixation surface and provided in a plurality of the posts located in an upstream side of the support structure in a rotational direction of the rotor; and
a second support structure fixing portion configured to fix the support structure to the post fixation surface and provided in a plurality of the posts located in a downstream side of the support structure in a rotational direction of the rotor,
wherein a height of the apex portion of the radiator unit from the post fixation surface is smaller than a distance between the first and second support structure fixing portions.

14. The cooler according to claim 12, further comprising:
a first fixation seat fixing portion configured to fix the fixation seat to the fixation seat fixing surface and provided in the frame structure located in an upstream side of the fixation seat in a rotational direction of the rotor; and
a second fixation seat fixing portion configured to fix the fixation seat to the fixation seat fixing surface and provided in the frame structure located in a downstream side of the fixation seat in a rotational direction of the rotor,
wherein a height of the apex portion of the radiator unit from the fixation seat fixing surface is smaller than a distance between the first and second fixation seat fixing portions.

15. The cooler according to claim 12, wherein
the radiator unit includes a plurality of radiators connected in parallel with the circulation pump.

* * * * *